US010517942B2

(12) United States Patent
Berman et al.

(10) Patent No.: US 10,517,942 B2
(45) Date of Patent: Dec. 31, 2019

(54) POLYPEPTIDE GLYCOPEPTIDE FRAGMENTS FROM THE V1/V2 AND V3 DOMAINS OF THE HIV-1 ENVELOPE PROTEIN GP 120

(71) Applicant: The Regents of the University of California, Oakland, CA (US)

(72) Inventors: Phillip Berman, Santa Cruz, CA (US); Rachel Doran, Santa Cruz, CA (US); Gabriel Byrne, Santa Cruz, CA (US); Rebecca Dubois, Santa Cruz, CA (US); Javier Morales, Santa Cruz, CA (US); Bin Yu, Santa Cruz, CA (US); Gerardo Perez, Santa Cruz, CA (US); Kathryn Mesa, Santa Cruz, CA (US); David Alexander, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/741,981

(22) PCT Filed: Aug. 1, 2016

(86) PCT No.: PCT/US2016/045023
§ 371 (c)(1),
(2) Date: Jan. 4, 2018

(87) PCT Pub. No.: WO2017/023857
PCT Pub. Date: Feb. 9, 2017

(65) Prior Publication Data
US 2019/0091326 A1    Mar. 28, 2019

Related U.S. Application Data

(60) Provisional application No. 62/200,014, filed on Aug. 1, 2015.

(51) Int. Cl.
*A61K 39/21* (2006.01)
*C07K 14/005* (2006.01)
*A61K 39/12* (2006.01)
*A61K 39/00* (2006.01)

(52) U.S. Cl.
CPC .............. *A61K 39/21* (2013.01); *A61K 39/12* (2013.01); *C07K 14/005* (2013.01); *A61K 2039/545* (2013.01); *A61K 2039/575* (2013.01); *C12N 2740/16122* (2013.01); *C12N 2740/16134* (2013.01)

(58) Field of Classification Search
CPC ............ C07K 16/1063; C07K 2317/34; C07K 16/1045; A61K 39/00; A61K 39/12; A61K 39/21
See application file for complete search history.

(56) References Cited

U.S. PATENT DOCUMENTS

| 7,847,085 B2 * | 12/2010 | Zolla-Pazner | A61K 39/21 424/188.1 |
|---|---|---|---|
| 2003/0229214 A1 | 12/2003 | Shiver et al. | |
| 2015/0175679 A1 | 6/2015 | Pinter | |

FOREIGN PATENT DOCUMENTS

WO    WO 2014/043220    3/2014

OTHER PUBLICATIONS

Rober-Guroff et al. J. Virol. 1998, vol. 72, pp. 10275-10280.*
PLOS Pathog. May 11, 2015, (5), p. 1-34.*
Bonsignori, et al.; "Analysis of a clonal lineage of HIV-1 envelope V2/V3 conformational epitope-specific broadly neutralizing antibodies and their inferred unmutated common ancestors"; J. Virol.; vol. 85, No. 19, pp. 9998-10009 (Oct. 2011).
Morales, et al.; "HIV-1 Envelope Proteins and V1/V2 Domain Scaffolds with Mannose-5 to Improve the Magnitude and Quality of Protective Antibody Responses to HIV-1"; J. Biol. Chem.; vol. 289, No. 30, pp. 20526-20542 (Jul. 25, 2014).

* cited by examiner

*Primary Examiner* — Bao Q Li
(74) *Attorney, Agent, or Firm* — Shweta Chandra; Bozicevic, Field & Francis LLP

(57) ABSTRACT

Creation of HIV-1 vaccine immunogens based on glycopeptide scaffolds containing sequences from the V1/V2/V3 and C3 domains of HIV-1 gp120 that is able to bind multiple broadly neutralizing antibodies when expressed in mammalian cells that incorporate mannose-5 and mannose-9 glycans.

17 Claims, 15 Drawing Sheets

Specification includes a Sequence Listing.

A. Diagram of the V1/V2 scaffolds

Fig. 1. (continued)
B. N-linked glycans on normal and GnTI⁻ 293 HEK cells
Normal 293                          GnTI⁻
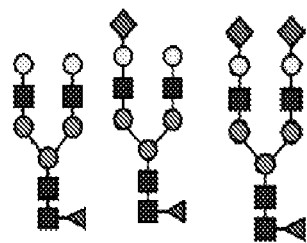                
Hybrid and Complex                  Mannose-5

Fig. 4.
A. A244 V1/V2 Wildtype (GnTI⁻)
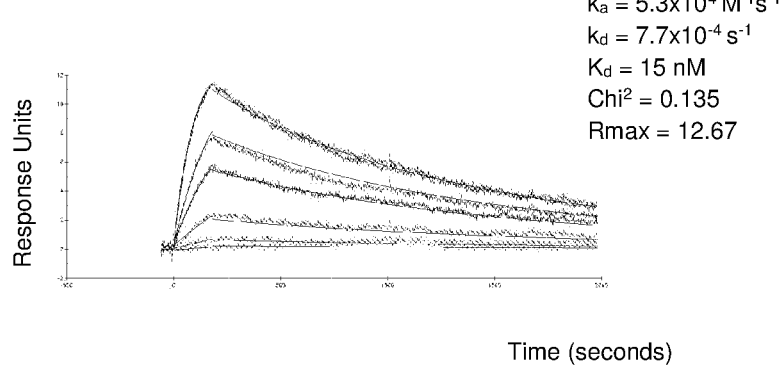
$k_a = 5.3 \times 10^4 \, M^{-1}s^{-1}$
$k_d = 7.7 \times 10^{-4} \, s^{-1}$
$K_d = 15 \, nM$
$Chi^2 = 0.135$
$Rmax = 12.67$
Time (seconds)
B. A244 V1/V2 engineered (293F)
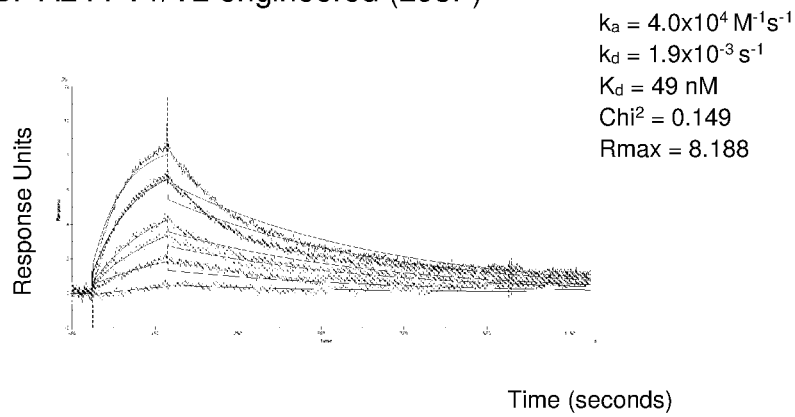
$k_a = 4.0 \times 10^4 \, M^{-1}s^{-1}$
$k_d = 1.9 \times 10^{-3} \, s^{-1}$
$K_d = 49 \, nM$
$Chi^2 = 0.149$
$Rmax = 8.188$
Time (seconds)
C. ZM233 V1/V2 engineered (293F)
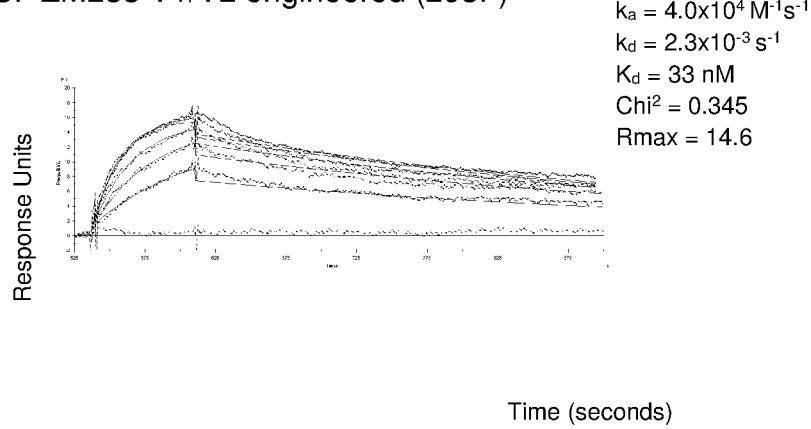
$k_a = 4.0 \times 10^4 \, M^{-1}s^{-1}$
$k_d = 2.3 \times 10^{-3} \, s^{-1}$
$K_d = 33 \, nM$
$Chi^2 = 0.345$
$Rmax = 14.6$
Time (seconds)

Fig. 5. (also referred to as Table S1). Listing of amino acid sequence and clade of wildtype and engineered V1/V2 scaffolds used for PG9 binding studies.

| | Scaffold | Clade | V1/V2 sequence |
|---|---|---|---|
| Wildtype | 108060 | B | LKPCVKLTPLCVTLNCTDKLRNDAFGVNNTMEGEMKNCSFNTTTSLRDKIQKEYALFYKLDVVQIKNNNNSNYTSYRLINCNTSVITQACPK |
| | MN | B | LKPCVKLTPLCVTLNCTDLRNTTNTNNSTDNNNSKSEGTIKGGEMKNCSFNITTSIGDKMQKEYALLYKLDIEPIDNDSTSYRLISCNTSVITQACPK |
| | JRFL-E168K | B | LKPCVKLTPLCVTLNCKDVNATNTTNDSEGTMERGEIKNCSFNITTSIRDKVQKEYALFYKLDVVPIDNNNTSYRLISCDTSVITQACPK |
| | A244 | AE | VKLTPPCVTLHCTNANLTKANLTNVNNRTNVSNIIGNITDEVRNCSFNMTTELRDKKQKVHALFYKLDIVPIEDNNDSSEYRLINCNTSVIKQA |
| | ZM233 | C | LKPCVKLTPLCVTLDCSTYNNTHNISKEMKICSFNMTTELRDKKRKVNVLFYKLDLVPLTNSSNTTNYRLISCNTSTITQACPK |
| | Bal.01 | B | LKPCVKLTPLCVTLNCTDLRNATSRNVTNTTSSSRGMVGGGEMKNCSFNITTGIRGKVQKEYALFYELDIVPIDNKIDRYRLISCNTSVITQACPK |
| | CAP.45 | C | LKPCVKLTPLCVTLRCTNATINGSLTEEVKNCSFNITTELRDKKQKAYALFYRPDVVPLNKNSPSGNSSEYILINCNTSTITQACPK |
| | ZM109 | C | LKPCVKLTPLCVTLNCTSPAAHNESETRVKHCSFNITTDVKDRKQKVNATFYDLDIVPLSSSDNSSNSSLYRLISCNTSTITQACPK |
| | ZM197 | C | LKPCVKLTPLCVTLNCSDATSNTTKNATNTNTTSTDNRNATSNDTEMKGEIKDCTFNITTEVRDRKTKQRALFYKLDVVPLEEEKNSSSKNSSYKEYRLISCNTSTITQACPK |
| Engineered | 108060.eng1 | B | LKPCVKLTPLCVTLNCTDKLRNDAFGVNNTMEGEMKICSFNMTTGLRGKKQKVYALFYKLDVVQIKNNNNSNYTSYRLINCNTSVITQACPK |
| | 108060.eng2 | B | LKPCVKLTPLCVTLNCTDKLRNDAFGVNNTMEGEMKICSFNMTTPGRDKKQKVYALFYKLDVVQIKNNNNSNYTSYRLINCNTSVITQACPK |
| | MN.eng1 | B | LKPCVKLTPLCVTLNCADLRNTTNNNAKSEGTIKGGEMKICSFNMTTGIGGKKQKVYALLYKLDIEPIDNDSTSYRLISCNTSVITQACPK |
| | JRFL-E168K.eng1 | B | LKPCVKLTPLCVTLNCKDVNATNTANDAEGTMERGEIKICSFNMTTGIRGKKQKVYALFYKLDVVPIDNNNTSYRLISCDTSVITQACPK |
| | A244.eng1 | AE | VKLTPPCVTLHCTNANLTKANLTNVNNRTNVSNIIGNITDEVRICSFNMTTGLRGKKQKVHALFYKLDIVPIEDNNDSSEYRLINCNTSVIKQA* |
| | ZM233.eng1 | C | LKPCVKLTPLCVTLDCSTYNNTHNISKEMKICSFNMTTGLRGKKRKVNVLFYKLDLVPLTNSSNTTNYRLISCNTSTITQACPK |

Fig. 6. (also referred to as Table S2). Summary of EC50s for PG9 binding to wildtype and engineered V1/V2 scaffolds determined by ELISA.

|  |  | PG9 binding ($EC_{50}$) | |
|---|---|---|---|
|  |  | 293 | GnTI- |
|  | V1V2 scaffold | $EC_{50}$ in ng/mL | $EC_{50}$ in ng/mL |
| Wildtype | 108060 V1/V2 wt | >10,000 | >10,000 |
|  | MN V1/V2 wt | >10,000 | >10,000 |
|  | JRFL-E168K V1/V2 wt | >10,000 | >10,000 |
|  | A244 V1/V2 wt | 893.5 | 0.7409 |
|  | ZM233 V1/V2 wt | 77.05 | 9.508 |
|  | Bal.01 V1/V2 wt | 853.3 | 80.22 |
|  | CAP.45 V1/V2 wt | 312.3 | 52.65 |
|  | ZM109 V1/V2 wt | 517 | 14.3 |
|  | ZM197 V1/V2 wt | 2740 | 30.27 |
| Engineered | 108060 V1/V2 I169K | >10,000 | 678.8 |
|  | 108060 V1/V2 I169K/E172V | >10,000 | 113.2 |
|  | 108060 I169K/E172V/T161M/N156I | 599.2 | 28.1 |
|  | 108060 V1/V2.eng1* | 93.03 | 6.846 |
|  | 108060 V1/V2.eng2** | 155.7 | 8.345 |
|  | MN V1/V2.eng1* | 27.43 | 7.965 |
|  | JRFL-E168K V1/V2.eng1* | 47.29 | 12.99 |
|  | A244 V1/V2.eng1* | 99.02 | 4.063 |
|  | ZM233 V1/V2.eng1* | 2.27 | 8.503 |

*eng1 = I169K/E172V/T161M/N156I/S164G/D167G
**eng2 = I169K/E172V/T161M/N156I/S164P/L165G Fig. 7. (also referred to as Fig. S1). Binding of PG9 to additional wildtype V1/V2 scaffolds produced in normal and GnTI- 293 HEK cells as measured by ELISA.
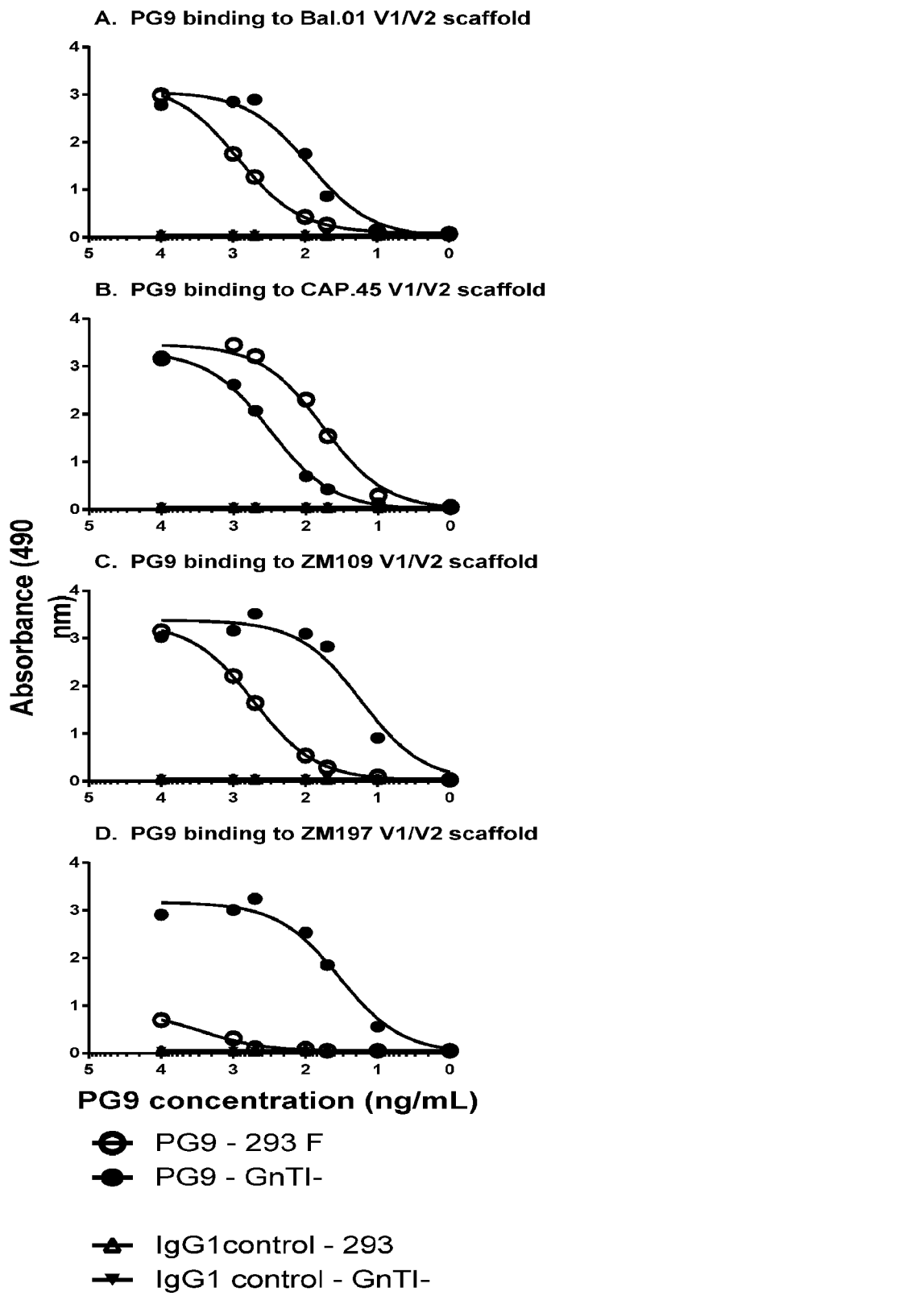

Fig. 8. (also referred to as Fig. S2). SDS-PAGE analysis of V1/V2 scaffolds used for PG9 binding studies.
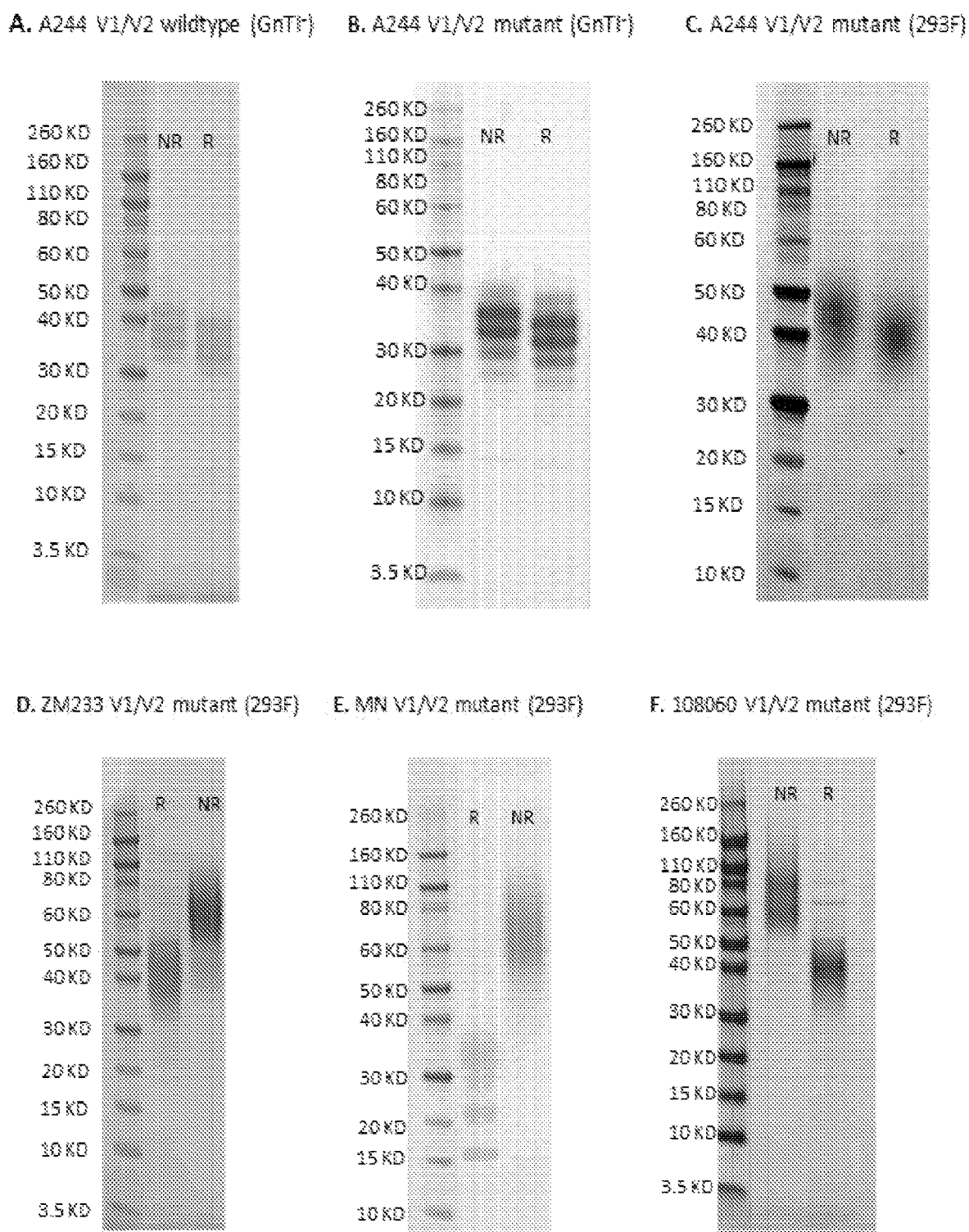

Fig. 9. (previously fig 5)

The initial two scaffolds (UCSC 912 and UCSC 913) differed by the addition of an extra disulfide (UCSC913) between the V3 crown and the connecting peptide between the B and C strands of the V1/V2 domain Fig. 10. (previously fig 6)

Fig. 11 (previously fig 7)
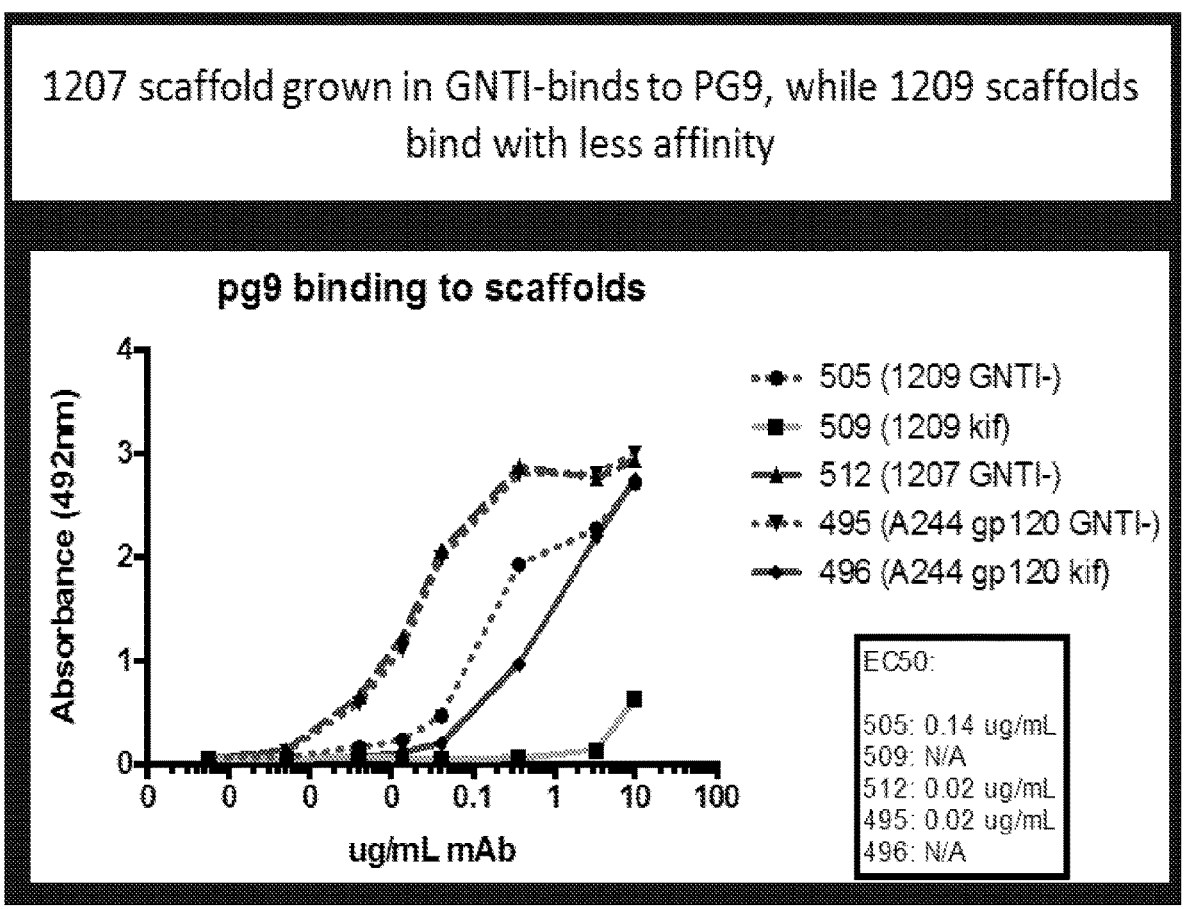

Fig. 12 (previously fig 8)
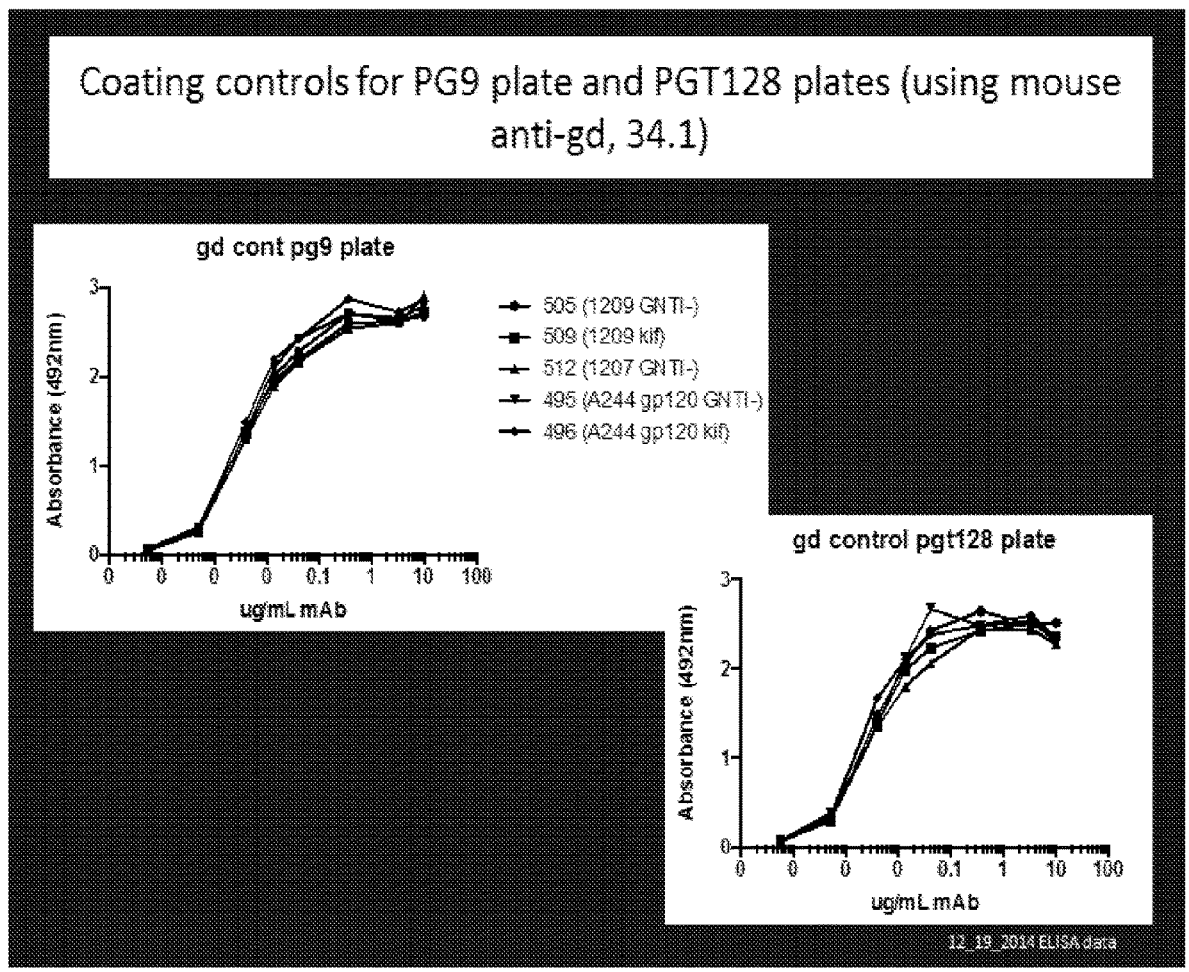

Fig. 13 (previously fig 9)

Summary of V1/V2/V3/C3 scaffolds without engineered disulfide bridges binding to bn-Mabs

| Family | bN-mAb | A244 GNTI- | A244 Kif | 912 (GNTI-) | 912 Kif | 1207 (GNTI-) | 1207 Kif | 1207 Mixed Batch Culture |
|---|---|---|---|---|---|---|---|---|
| PG9 | PG9 | + | + | + | - | + | - | + |
|  | CHO1 | + | + | + | + | + | + | + |
|  | CHO3 | + | + | + | + | + | + | + |
|  | VRC26.08 | + | + | + | + | + | + | + |
| PGT145 | PGT 145 | + | + | - | - | - | - | - |
| PGT121 | pgt121 | - | - | - | - | + | + | + |
|  | pgt122 | - | - | - | - | + | + | + |
| PGT125 | pgt 125 | + | + | - | + | - | + | + |
|  | pgt 128 | + | + | - | + | - | + | + |
|  | pgt 130 | + | ND | - | + | - | + | + |
| PGT135 | pgt 135 | + | + | - | - | - | - | - |

SEQUENCE LISTING

```
<160> NUMBER OF SEQ ID NOS: 35

<210> SEQ ID NO 1
<211> LENGTH: 675
<212> TYPE: DNA
<213> ORGANISM: Artificial sequence
<220> FEATURE:
<223> OTHER INFORMATION: synthetic sequence

<400> SEQUENCE: 1
atgggcggag ccgccgctag actgggagcc gtgattctgt tcgtcgtgat cgtgggcctg      60
catggcgtgc gggcaaaata tgccctggcc gatgccagcc tgaagatggc cgaccccaac     120
cggttcagag gcaaggacct gcccgtgctg gatcagctgc tggaggtacc actgaagccc     180
gccgtgaagc tgaccccctcc ttgtgtgacc ctgcactgca ccaacgccaa cctgaccaag     240
gccaatctga caaacgtgaa caaccggacc aacgtgtcca acatcatcgg caacatcacc     300
```

```
gacgaagtgc ggaactgcag cttcaacatg accaccgagc tgcgggacaa gaaacagaag      360
gtgcacgccc tgttctacaa gctggacatc gtgcccatcg aggacaacaa cgacagcagc      420
gagtaccggc tgatcaactg caacaccagc gtgatcaagc aggccgctcc caagatcagc      480
ttcgaccctg gcggcggagg atctggcgga ggcggaagtg gcggaggggg ctctgtgatc      540
aattgcaccc ggcccagcaa caacaccaga accagcatca ccatcggccc aggccaggtg      600
ttctaccgga ccggcgatat catcggagac atccggaagg cctactgcga gatcaacggc      660
accgagtgga actga                                                       675
```

```
<210> SEQ ID NO 2
<211> LENGTH: 675
<212> TYPE: DNA
<213> ORGANISM: Artificial sequence
<220> FEATURE:
<223> OTHER INFORMATION: synthetic sequence

<400> SEQUENCE: 2
atgggcggag ccgccgctag actgggagcc gtgattctgt tcgtcgtgat cgtgggcctg       60
catggcgtgc ggggcaaata tgccctggcc gatgccagcc tgaagatggc cgaccccaac      120
cggttcagag gcaaggacct gcccgtgctg atcagctgc tggaggtacc actgaagccc      180
gccgtgaagc tgaccccctcc ttgtgtgacc ctgcactgca ccaacgccaa cctgaccaag      240
gccaatctga caaacgtgaa caaccggacc aacgtgtcca acatcatcgg caacatcacc      300
gacgaagtgc ggaactgcag cttcaacatg acctgcgagc tgcgggacaa gaaacagaag      360
gtgcacgccc tgttctacaa gctggacatc gtgcccatcg aggacaacaa cgacagcagc      420
gagtaccggc tgatcaactg caacaccagc gtgatcaagc aggccgctcc caagatcagc      480
ttcgaccctg gcggcggagg atctggcgga ggcggaagtg gcggaggggg ctctgtgatc      540
aattgcaccc ggcccagcaa caacaccaga accagcatca cctgtggccc aggccaggtg      600
ttctaccgga ccggcgatat catcggagac atccggaagg cctactgcga gatcaacggc      660
accgagtgga actga                                                       675
```

```
<210> SEQ ID NO 3
<211> LENGTH: 224
<212> TYPE: PRT
<213> ORGANISM: Artificial sequence
<220> FEATURE:
<223> OTHER INFORMATION: synthetic sequence

<400> SEQUENCE: 3

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Leu Glu Val Pro Leu Lys Pro Ala Val Lys Leu
    50                  55                  60

Thr Pro Pro Cys Val Thr Leu His Cys Thr Asn Ala Asn Leu Thr Lys
65                  70                  75                  80

Ala Asn Leu Thr Asn Val Asn Asn Arg Thr Asn Val Ser Asn Ile Ile
                85                  90                  95

Gly Asn Ile Thr Asp Glu Val Arg Asn Cys Ser Phe Asn Met Thr Cys
            100                 105                 110
```

```
Glu Leu Arg Asp Lys Lys Gln Lys Val His Ala Leu Phe Tyr Lys Leu
        115                 120                 125

Asp Ile Val Pro Ile Glu Asp Asn Asn Asp Ser Ser Glu Tyr Arg Leu
130                 135                 140

Ile Asn Cys Asn Thr Ser Val Ile Lys Gln Ala Ala Pro Lys Ile Ser
145                 150                 155                 160

Phe Asp Pro Gly Gly Gly Ser Gly Gly Gly Ser Gly Gly
                165                 170                 175

Gly Ser Val Ile Asn Cys Thr Arg Pro Ser Asn Asn Thr Arg Thr Ser
        180                 185                 190

Ile Thr Cys Gly Pro Gly Gln Val Phe Tyr Arg Thr Gly Asp Ile Ile
        195                 200                 205

Gly Asp Ile Arg Lys Ala Tyr Cys Asn Ile Ser Gly Thr Glu Trp Asn
        210                 215                 220
```

<210> SEQ ID NO 4
<211> LENGTH: 133
<212> TYPE: PRT
<213> ORGANISM: Artificial sequence
<220> FEATURE:
<223> OTHER INFORMATION: synthetic sequence

<400> SEQUENCE: 4

```
Lys Tyr Ala Leu Ala Asp Ala Ser Leu Lys Met Ala Asp Pro Asn Arg
1               5                   10                  15

Phe Arg Gly Lys Asp Leu Pro Val Leu Asp Gln Leu Leu Glu Val Pro
            20                  25                  30

Leu Lys Pro Cys Val Lys Leu Thr Pro Pro Cys Val Thr Leu His Cys
        35                  40                  45

Thr Asn Ala Asn Leu Thr Lys Ala Asn Leu Thr Asn Val Asn Asn Arg
    50                  55                  60

Thr Asn Val Ser Asn Ile Ile Gly Asn Ile Thr Asp Glu Val Arg Asn
65                  70                  75                  80

Cys Ser Phe Asn Met Thr Thr Glu Leu Arg Asp Lys Lys Gln Lys Val
                85                  90                  95

His Ala Leu Phe Tyr Lys Leu Asp Ile Val Pro Ile Glu Asp Asn Asn
            100                 105                 110

Asp Ser Ser Glu Tyr Arg Leu Ile Asn Cys Asn Thr Ser Val Ile Lys
        115                 120                 125

Gln Ala Cys Pro Lys
    130
```

<210> SEQ ID NO 5
<211> LENGTH: 31
<212> TYPE: PRT
<213> ORGANISM: Artificial sequence
<220> FEATURE:
<223> OTHER INFORMATION: synthetic sequence

<400> SEQUENCE: 5

```
Lys Gly Glu Ile Lys Asn Cys Ser Phe Asn Ile Ser Thr Ser Ile Arg
1               5                   10                  15

Gly Lys Val Gln Lys Glu Tyr Ala Phe Phe Tyr Lys Leu Asp Ile
            20                  25                  30
```

<210> SEQ ID NO 6
<211> LENGTH: 31
<212> TYPE: PRT

```
<213> ORGANISM: Artificial sequence
<220> FEATURE:
<223> OTHER INFORMATION: synthetic sequence

<400> SEQUENCE: 6

Glu Gly Glu Met Lys Asn Cys Ser Phe Asn Thr Thr Thr Ser Leu Arg
1               5                   10                  15

Asp Lys Ile Gln Lys Glu Tyr Ala Leu Phe Tyr Lys Leu Asp Val
            20                  25                  30

<210> SEQ ID NO 7
<211> LENGTH: 31
<212> TYPE: PRT
<213> ORGANISM: Artificial sequence
<220> FEATURE:
<223> OTHER INFORMATION: synthetic sequence

<400> SEQUENCE: 7

Glu Gly Glu Met Lys Ile Cys Ser Phe Asn Met Thr Thr Gly Leu Arg
1               5                   10                  15

Gly Lys Lys Gln Lys Val Tyr Ala Leu Phe Tyr Lys Leu Asp Val
            20                  25                  30

<210> SEQ ID NO 8
<211> LENGTH: 31
<212> TYPE: PRT
<213> ORGANISM: Artificial sequence
<220> FEATURE:
<223> OTHER INFORMATION: synthetic sequence

<400> SEQUENCE: 8

Glu Gly Glu Met Lys Ile Cys Ser Phe Asn Met Thr Thr Pro Gly Arg
1               5                   10                  15

Asp Lys Lys Gln Lys Val Tyr Ala Leu Phe Tyr Lys Leu Asp Val
            20                  25                  30

<210> SEQ ID NO 9
<211> LENGTH: 31
<212> TYPE: PRT
<213> ORGANISM: Artificial sequence
<220> FEATURE:
<223> OTHER INFORMATION: synthetic sequence

<400> SEQUENCE: 9

Arg Gly Glu Ile Lys Asn Cys Ser Phe Asn Ile Thr Thr Ser Ile Arg
1               5                   10                  15

Asp Lys Val Gln Lys Glu Tyr Ala Leu Phe Tyr Lys Leu Asp Val
            20                  25                  30

<210> SEQ ID NO 10
<211> LENGTH: 31
<212> TYPE: PRT
<213> ORGANISM: Artificial sequence
<220> FEATURE:
<223> OTHER INFORMATION: synthetic sequence

<400> SEQUENCE: 10

Gly Gly Glu Met Lys Asn Cys Ser Phe Asn Ile Thr Thr Ser Ile Gly
1               5                   10                  15

Asp Lys Met Gln Lys Glu Tyr Ala Leu Leu Tyr Lys Leu Asp Ile
            20                  25                  30

<210> SEQ ID NO 11
<211> LENGTH: 31
```

```
<212> TYPE: PRT
<213> ORGANISM: Artificial sequence
<220> FEATURE:
<223> OTHER INFORMATION: synthetic sequence

<400> SEQUENCE: 11

Gly Gly Glu Met Lys Asn Cys Ser Phe Asn Ile Thr Thr Gly Ile Arg
1               5                   10                  15

Gly Lys Val Gln Lys Glu Tyr Ala Leu Phe Tyr Glu Leu Asp Ile
            20                  25                  30

<210> SEQ ID NO 12
<211> LENGTH: 31
<212> TYPE: PRT
<213> ORGANISM: Artificial sequence
<220> FEATURE:
<223> OTHER INFORMATION: synthetic sequence

<400> SEQUENCE: 12

Thr Glu Glu Val Lys Asn Cys Ser Phe Asn Ile Thr Thr Glu Leu Arg
1               5                   10                  15

Asp Lys Lys Gln Lys Ala Tyr Ala Leu Phe Tyr Arg Pro Asp Val
            20                  25                  30

<210> SEQ ID NO 13
<211> LENGTH: 31
<212> TYPE: PRT
<213> ORGANISM: Artificial sequence
<220> FEATURE:
<223> OTHER INFORMATION: synthetic sequence

<400> SEQUENCE: 13

Lys Gly Glu Ile Lys Asp Cys Thr Phe Asn Ile Thr Thr Glu Val Arg
1               5                   10                  15

Asp Arg Lys Thr Lys Gln Arg Ala Leu Phe Tyr Lys Leu Asp Val
            20                  25                  30

<210> SEQ ID NO 14
<211> LENGTH: 31
<212> TYPE: PRT
<213> ORGANISM: Artificial sequence
<220> FEATURE:
<223> OTHER INFORMATION: synthetic sequence

<400> SEQUENCE: 14

Glu Thr Arg Val Lys His Cys Ser Phe Asn Ile Thr Thr Asp Val Lys
1               5                   10                  15

Asp Arg Lys Gln Lys Val Asn Ala Thr Phe Tyr Asp Leu Asp Ile
            20                  25                  30

<210> SEQ ID NO 15
<211> LENGTH: 31
<212> TYPE: PRT
<213> ORGANISM: Artificial sequence
<220> FEATURE:
<223> OTHER INFORMATION: synthetic sequence

<400> SEQUENCE: 15

Thr Asp Glu Val Arg Asn Cys Ser Phe Asn Met Thr Thr Glu Leu Arg
1               5                   10                  15

Gly Lys Lys Gln Lys Val His Ala Leu Phe Tyr Lys Leu Asp Ile
            20                  25                  30

<210> SEQ ID NO 16
```

```
<211> LENGTH: 31
<212> TYPE: PRT
<213> ORGANISM: Artificial sequence
<220> FEATURE:
<223> OTHER INFORMATION: synthetic sequence

<400> SEQUENCE: 16

Thr Asp Glu Val Arg Ile Cys Ser Phe Asn Met Thr Thr Gly Leu Arg
1               5                   10                  15

Gly Lys Lys Gln Lys Val His Ala Leu Phe Tyr Lys Leu Asp Ile
            20                  25                  30

<210> SEQ ID NO 17
<211> LENGTH: 31
<212> TYPE: PRT
<213> ORGANISM: Artificial sequence
<220> FEATURE:
<223> OTHER INFORMATION: synthetic sequence

<400> SEQUENCE: 17

Ser Lys Glu Met Lys Ile Cys Ser Phe Asn Met Thr Thr Glu Leu Arg
1               5                   10                  15

Gly Lys Lys Arg Lys Val Asn Val Leu Phe Tyr Lys Leu Asp Leu
            20                  25                  30

<210> SEQ ID NO 18
<211> LENGTH: 31
<212> TYPE: PRT
<213> ORGANISM: Artificial sequence
<220> FEATURE:
<223> OTHER INFORMATION: synthetic sequence

<400> SEQUENCE: 18

Ser Lys Glu Met Lys Ile Cys Ser Phe Asn Met Thr Thr Gly Leu Arg
1               5                   10                  15

Gly Lys Lys Arg Lys Val Asn Val Leu Phe Tyr Lys Leu Asp Leu
            20                  25                  30

<210> SEQ ID NO 19
<211> LENGTH: 92
<212> TYPE: PRT
<213> ORGANISM: Artificial sequence
<220> FEATURE:
<223> OTHER INFORMATION: synthetic sequence

<400> SEQUENCE: 19

Leu Lys Pro Cys Val Lys Leu Thr Pro Leu Cys Val Thr Leu Asn Cys
1               5                   10                  15

Thr Asp Lys Leu Arg Asn Asp Ala Phe Gly Val Asn Asn Thr Met Glu
            20                  25                  30

Gly Glu Met Lys Asn Cys Ser Phe Asn Thr Thr Thr Ser Leu Arg Asp
        35                  40                  45

Lys Ile Gln Lys Glu Tyr Ala Leu Phe Tyr Lys Leu Asp Val Val Gln
    50                  55                  60

Ile Lys Asn Asn Asn Asn Ser Asn Tyr Thr Ser Tyr Arg Leu Ile Asn
65                  70                  75                  80

Cys Asn Thr Ser Val Ile Thr Gln Ala Cys Pro Lys
                85                  90

<210> SEQ ID NO 20
<211> LENGTH: 98
<212> TYPE: PRT
<213> ORGANISM: Artificial sequence
```

```
<220> FEATURE:
<223> OTHER INFORMATION: synthetic sequence

<400> SEQUENCE: 20

Leu Lys Pro Cys Val Lys Leu Thr Pro Leu Cys Val Thr Leu Asn Cys
1               5                   10                  15

Thr Asp Leu Arg Asn Thr Thr Asn Thr Asn Asn Ser Thr Asp Asn Asn
                20                  25                  30

Asn Ser Lys Ser Glu Gly Thr Ile Lys Gly Gly Glu Met Lys Asn Cys
            35                  40                  45

Ser Phe Asn Ile Thr Thr Ser Ile Gly Asp Lys Met Gln Lys Glu Tyr
        50                  55                  60

Ala Leu Leu Tyr Lys Leu Asp Ile Glu Pro Ile Asp Asn Asp Ser Thr
65                  70                  75                  80

Ser Tyr Arg Leu Ile Ser Cys Asn Thr Ser Val Ile Thr Gln Ala Cys
                    85                  90                  95

Pro Lys

<210> SEQ ID NO 21
<211> LENGTH: 98
<212> TYPE: PRT
<213> ORGANISM: Artificial sequence
<220> FEATURE:
<223> OTHER INFORMATION: synthetic sequence

<400> SEQUENCE: 21

Leu Lys Pro Cys Val Lys Leu Thr Pro Leu Cys Val Thr Leu Asn Cys
1               5                   10                  15

Thr Asp Leu Arg Asn Thr Thr Asn Thr Asn Asn Ser Thr Asp Asn Asn
                20                  25                  30

Asn Ser Lys Ser Glu Gly Thr Ile Lys Gly Gly Glu Met Lys Asn Cys
            35                  40                  45

Ser Phe Asn Ile Thr Thr Ser Ile Gly Asp Lys Met Gln Lys Glu Tyr
        50                  55                  60

Ala Leu Leu Tyr Lys Leu Asp Ile Glu Pro Ile Asp Asn Asp Ser Thr
65                  70                  75                  80

Ser Tyr Arg Leu Ile Ser Cys Asn Thr Ser Val Ile Thr Gln Ala Cys
                    85                  90                  95

Pro Lys

<210> SEQ ID NO 22
<211> LENGTH: 94
<212> TYPE: PRT
<213> ORGANISM: Artificial sequence
<220> FEATURE:
<223> OTHER INFORMATION: synthetic sequence

<400> SEQUENCE: 22

Val Lys Leu Thr Pro Pro Cys Val Thr Leu His Cys Thr Asn Ala Asn
1               5                   10                  15

Leu Thr Lys Ala Asn Leu Thr Asn Val Asn Asn Arg Thr Asn Val Ser
                20                  25                  30

Asn Ile Ile Gly Asn Ile Thr Asp Glu Val Arg Asn Cys Ser Phe Asn
            35                  40                  45

Met Thr Thr Glu Leu Arg Asp Lys Lys Gln Lys Val His Ala Leu Phe
        50                  55                  60

Tyr Lys Leu Asp Ile Val Pro Ile Glu Asp Asn Asn Asp Ser Ser Glu
65                  70                  75                  80
```

Tyr Arg Leu Ile Asn Cys Asn Thr Ser Val Ile Lys Gln Ala
            85                  90

<210> SEQ ID NO 23
<211> LENGTH: 84
<212> TYPE: PRT
<213> ORGANISM: Artificial sequence
<220> FEATURE:
<223> OTHER INFORMATION: synthetic sequence

<400> SEQUENCE: 23

Leu Lys Pro Cys Val Lys Leu Thr Pro Leu Cys Val Thr Leu Asp Cys
1               5                   10                  15

Ser Thr Tyr Asn Asn Thr His Asn Ile Ser Lys Glu Met Lys Ile Cys
            20                  25                  30

Ser Phe Asn Met Thr Thr Glu Leu Arg Asp Lys Arg Lys Val Asn
        35                  40                  45

Val Leu Phe Tyr Lys Leu Asp Leu Val Pro Leu Thr Asn Ser Ser Asn
    50                  55                  60

Thr Thr Asn Tyr Arg Leu Ile Ser Cys Asn Thr Ser Thr Ile Thr Gln
65                  70                  75                  80

Ala Cys Pro Lys

<210> SEQ ID NO 24
<211> LENGTH: 96
<212> TYPE: PRT
<213> ORGANISM: Artificial sequence
<220> FEATURE:
<223> OTHER INFORMATION: synthetic sequence

<400> SEQUENCE: 24

Leu Lys Pro Cys Val Lys Leu Thr Pro Leu Cys Val Thr Leu Asn Cys
1               5                   10                  15

Thr Asp Leu Arg Asn Ala Thr Ser Arg Asn Val Thr Asn Thr Thr Ser
            20                  25                  30

Ser Ser Arg Gly Met Val Gly Gly Glu Met Lys Asn Cys Ser Phe
        35                  40                  45

Asn Ile Thr Thr Gly Ile Arg Gly Lys Val Gln Lys Glu Tyr Ala Leu
    50                  55                  60

Phe Tyr Glu Leu Asp Ile Val Pro Ile Asp Asn Lys Ile Asp Arg Tyr
65                  70                  75                  80

Arg Leu Ile Ser Cys Asn Thr Ser Val Ile Thr Gln Ala Cys Pro Lys
            85                  90                  95

<210> SEQ ID NO 25
<211> LENGTH: 87
<212> TYPE: PRT
<213> ORGANISM: Artificial sequence
<220> FEATURE:
<223> OTHER INFORMATION: synthetic sequence

<400> SEQUENCE: 25

Leu Lys Pro Cys Val Lys Leu Thr Pro Leu Cys Val Thr Leu Arg Cys
1               5                   10                  15

Thr Asn Ala Thr Ile Asn Gly Ser Leu Thr Glu Glu Val Lys Asn Cys
            20                  25                  30

Ser Phe Asn Ile Thr Thr Glu Leu Arg Asp Lys Lys Gln Lys Ala Tyr
        35                  40                  45

Ala Leu Phe Tyr Arg Pro Asp Val Val Pro Leu Asn Lys Asn Ser Pro

```
                50                  55                  60
Ser Gly Asn Ser Ser Glu Tyr Ile Leu Ile Asn Cys Asn Thr Ser Thr
 65                  70                  75                  80

Ile Thr Gln Ala Cys Pro Lys
                 85

<210> SEQ ID NO 26
<211> LENGTH: 87
<212> TYPE: PRT
<213> ORGANISM: Artificial sequence
<220> FEATURE:
<223> OTHER INFORMATION: synthetic sequence

<400> SEQUENCE: 26

Leu Lys Pro Cys Val Lys Leu Thr Pro Leu Cys Val Thr Leu Asn Cys
 1               5                  10                  15

Thr Ser Pro Ala Ala His Asn Glu Ser Glu Thr Arg Val Lys His Cys
                20                  25                  30

Ser Phe Asn Ile Thr Thr Asp Val Lys Asp Arg Lys Gln Lys Val Asn
                35                  40                  45

Ala Thr Phe Tyr Asp Leu Asp Ile Val Pro Leu Ser Ser Ser Asp Asn
     50                  55                  60

Ser Ser Asn Ser Ser Leu Tyr Arg Leu Ile Ser Cys Asn Thr Ser Thr
 65                  70                  75                  80

Ile Thr Gln Ala Cys Pro Lys
                 85

<210> SEQ ID NO 27
<211> LENGTH: 113
<212> TYPE: PRT
<213> ORGANISM: Artificial sequence
<220> FEATURE:
<223> OTHER INFORMATION: synthetic sequence

<400> SEQUENCE: 27

Leu Lys Pro Cys Val Lys Leu Thr Pro Leu Cys Val Thr Leu Asn Cys
 1               5                  10                  15

Ser Asp Ala Thr Ser Asn Thr Thr Lys Asn Ala Thr Asn Thr Asn Thr
                20                  25                  30

Thr Ser Thr Asp Asn Arg Asn Ala Thr Ser Asn Asp Thr Glu Met Lys
                35                  40                  45

Gly Glu Ile Lys Asp Cys Thr Phe Asn Ile Thr Thr Glu Val Arg Asp
     50                  55                  60

Arg Lys Thr Lys Gln Arg Ala Leu Phe Tyr Lys Leu Asp Val Val Pro
 65                  70                  75                  80

Leu Glu Glu Glu Lys Asn Ser Ser Ser Lys Asn Ser Ser Tyr Lys Glu
                85                  90                  95

Tyr Arg Leu Ile Ser Cys Asn Thr Ser Thr Ile Thr Gln Ala Cys Pro
                100                 105                 110

Lys

<210> SEQ ID NO 28
<211> LENGTH: 92
<212> TYPE: PRT
<213> ORGANISM: Artificial sequence
<220> FEATURE:
<223> OTHER INFORMATION: synthetic sequence

<400> SEQUENCE: 28
```

```
Leu Lys Pro Cys Val Lys Leu Thr Pro Leu Cys Val Thr Leu Asn Cys
1               5                   10                  15

Thr Asp Lys Leu Arg Asn Asp Ala Phe Gly Val Asn Asn Thr Met Glu
            20                  25                  30

Gly Glu Met Lys Ile Cys Ser Phe Asn Met Thr Thr Gly Leu Arg Gly
            35                  40                  45

Lys Lys Gln Lys Val Tyr Ala Leu Phe Tyr Lys Leu Asp Val Val Gln
            50                  55                  60

Ile Lys Asn Asn Asn Ser Asn Tyr Thr Ser Tyr Arg Leu Ile Asn
65                  70                  75                  80

Cys Asn Thr Ser Val Ile Thr Gln Ala Cys Pro Lys
                85                  90
```

<210> SEQ ID NO 29
<211> LENGTH: 92
<212> TYPE: PRT
<213> ORGANISM: Artificial sequence
<220> FEATURE:
<223> OTHER INFORMATION: synthetic sequence

<400> SEQUENCE: 29

```
Leu Lys Pro Cys Val Lys Leu Thr Pro Leu Cys Val Thr Leu Asn Cys
1               5                   10                  15

Thr Asp Lys Leu Arg Asn Asp Ala Phe Gly Val Asn Asn Thr Met Glu
            20                  25                  30

Gly Glu Met Lys Ile Cys Ser Phe Asn Met Thr Thr Pro Gly Arg Asp
            35                  40                  45

Lys Lys Gln Lys Val Tyr Ala Leu Phe Tyr Lys Leu Asp Val Val Gln
            50                  55                  60

Ile Lys Asn Asn Asn Ser Asn Tyr Thr Ser Tyr Arg Leu Ile Asn
65                  70                  75                  80

Cys Asn Thr Ser Val Ile Thr Gln Ala Cys Pro Lys
                85                  90
```

<210> SEQ ID NO 30
<211> LENGTH: 91
<212> TYPE: PRT
<213> ORGANISM: Artificial sequence
<220> FEATURE:
<223> OTHER INFORMATION: synthetic sequence

<400> SEQUENCE: 30

```
Leu Lys Pro Cys Val Lys Leu Thr Pro Leu Cys Val Thr Leu Asn Cys
1               5                   10                  15

Ala Asp Leu Arg Asn Thr Thr Asn Asn Ala Lys Ser Glu Gly Thr
            20                  25                  30

Ile Lys Gly Gly Glu Met Lys Ile Cys Ser Phe Asn Met Thr Thr Gly
            35                  40                  45

Ile Gly Gly Lys Lys Gln Lys Val Tyr Ala Leu Leu Tyr Lys Leu Asp
            50                  55                  60

Ile Glu Pro Ile Asp Asn Asp Ser Thr Ser Tyr Arg Leu Ile Ser Cys
65                  70                  75                  80

Asn Thr Ser Val Ile Thr Gln Ala Cys Pro Lys
                85                  90
```

<210> SEQ ID NO 31
<211> LENGTH: 90
<212> TYPE: PRT
<213> ORGANISM: Artificial sequence
<220> FEATURE:
<223> OTHER INFORMATION: synthetic sequence

<400> SEQUENCE: 31

Leu Lys Pro Cys Val Lys Leu Thr Pro Leu Cys Val Thr Leu Asn Cys
1               5                   10                  15

Lys Asp Val Asn Ala Thr Asn Thr Ala Asn Asp Ala Glu Gly Thr Met
            20                  25                  30

Glu Arg Gly Glu Ile Lys Ile Cys Ser Phe Asn Met Thr Thr Gly Ile
        35                  40                  45

Arg Gly Lys Lys Gln Lys Val Tyr Ala Leu Phe Tyr Lys Leu Asp Val
    50                  55                  60

Val Pro Ile Asp Asn Asn Asn Thr Ser Tyr Arg Leu Ile Ser Cys Asp
65                  70                  75                  80

Thr Ser Val Ile Thr Gln Ala Cys Pro Lys
                85                  90

<210> SEQ ID NO 32
<211> LENGTH: 94
<212> TYPE: PRT
<213> ORGANISM: Artificial sequence
<220> FEATURE:
<223> OTHER INFORMATION: synthetic sequence

<400> SEQUENCE: 32

Val Lys Leu Thr Pro Pro Cys Val Thr Leu His Cys Thr Asn Ala Asn
1               5                   10                  15

Leu Thr Lys Ala Asn Leu Thr Asn Val Asn Asn Arg Thr Asn Val Ser
            20                  25                  30

Asn Ile Ile Gly Asn Ile Thr Asp Glu Val Arg Ile Cys Ser Phe Asn
        35                  40                  45

Met Thr Thr Gly Leu Arg Gly Lys Lys Gln Lys Val His Ala Leu Phe
    50                  55                  60

Tyr Lys Leu Asp Ile Val Pro Ile Glu Asp Asn Asn Asp Ser Ser Glu
65                  70                  75                  80

Tyr Arg Leu Ile Asn Cys Asn Thr Ser Val Ile Lys Gln Ala
                85                  90

<210> SEQ ID NO 33
<211> LENGTH: 84
<212> TYPE: PRT
<213> ORGANISM: Artificial sequence
<220> FEATURE:
<223> OTHER INFORMATION: synthetic sequence

<400> SEQUENCE: 33

Leu Lys Pro Cys Val Lys Leu Thr Pro Leu Cys Val Thr Leu Asp Cys
1               5                   10                  15

Ser Thr Tyr Asn Asn Thr His Asn Ile Ser Lys Glu Met Lys Ile Cys
            20                  25                  30

Ser Phe Asn Met Thr Thr Gly Leu Arg Gly Lys Lys Arg Lys Val Asn
        35                  40                  45

Val Leu Phe Tyr Lys Leu Asp Leu Val Pro Leu Thr Asn Ser Ser Asn
    50                  55                  60

Thr Thr Asn Tyr Arg Leu Ile Ser Cys Asn Thr Ser Thr Ile Thr Gln
65                  70                  75                  80

Ala Cys Pro Lys

<210> SEQ ID NO 34
<211> LENGTH: 224
<212> TYPE: PRT
<213> ORGANISM: Artificial sequence
<220> FEATURE:
<223> OTHER INFORMATION: synthetic sequence

<400> SEQUENCE: 34

```
Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Leu Glu Val Pro Leu Lys Pro Ala Val Lys Leu
    50                  55                  60

Thr Pro Pro Cys Val Thr Leu His Cys Thr Asn Ala Asn Leu Thr Lys
65                  70                  75                  80

Ala Asn Leu Thr Asn Val Asn Asn Arg Thr Asn Val Ser Asn Ile Ile
                85                  90                  95

Gly Asn Ile Thr Asp Glu Val Arg Asn Cys Ser Phe Asn Met Thr Thr
            100                 105                 110

Glu Leu Arg Asp Lys Lys Gln Lys Val His Ala Leu Phe Tyr Lys Leu
        115                 120                 125

Asp Ile Val Pro Ile Glu Asp Asn Asn Asp Ser Ser Glu Tyr Arg Leu
    130                 135                 140

Ile Asn Cys Asn Thr Ser Val Ile Lys Gln Ala Ala Pro Lys Ile Ser
145                 150                 155                 160

Phe Asp Pro Gly Gly Gly Gly Ser Gly Gly Gly Ser Gly Gly Gly Gly
                165                 170                 175

Gly Ser Val Ile Asn Cys Thr Arg Pro Ser Asn Asn Thr Arg Thr Ser
            180                 185                 190

Ile Thr Ile Gly Pro Gly Gln Val Phe Tyr Arg Thr Gly Asp Ile Ile
        195                 200                 205

Gly Asp Ile Arg Lys Ala Tyr Cys Glu Ile Asn Gly Thr Glu Trp Asn
    210                 215                 220
```

<210> SEQ ID NO 35
<211> LENGTH: 224
<212> TYPE: PRT
<213> ORGANISM: Artificial sequence
<220> FEATURE:
<223> OTHER INFORMATION: synthetic sequence

<400> SEQUENCE: 35

```
Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Leu Glu Val Pro Leu Lys Pro Ala Val Lys Leu
    50                  55                  60

Thr Pro Pro Cys Val Thr Leu His Cys Thr Asn Ala Asn Leu Thr Lys
65                  70                  75                  80

Ala Asn Leu Thr Asn Val Asn Asn Arg Thr Asn Val Ser Asn Ile Ile
                85                  90                  95
```

-continued

```
Gly Asn Ile Thr Asp Glu Val Arg Asn Cys Ser Phe Asn Met Thr Cys
            100                 105                 110

Glu Leu Arg Asp Lys Lys Gln Lys Val His Ala Leu Phe Tyr Lys Leu
        115                 120                 125

Asp Ile Val Pro Ile Glu Asp Asn Asn Asp Ser Ser Glu Tyr Arg Leu
    130                 135                 140

Ile Asn Cys Asn Thr Ser Val Ile Lys Gln Ala Ala Pro Lys Ile Ser
145                 150                 155                 160

Phe Asp Pro Gly Gly Gly Gly Ser Gly Gly Gly Gly Ser Gly Gly Gly
                165                 170                 175

Gly Ser Val Ile Asn Cys Thr Arg Pro Ser Asn Asn Thr Arg Thr Ser
            180                 185                 190

Ile Thr Cys Gly Pro Gly Gln Val Phe Tyr Arg Thr Gly Asp Ile Ile
        195                 200                 205

Gly Asp Ile Arg Lys Ala Tyr Cys Glu Ile Asn Gly Thr Glu Trp Asn
    210                 215                 220
```

POLYPEPTIDE GLYCOPEPTIDE FRAGMENTS FROM THE V1/V2 AND V3 DOMAINS OF THE HIV-1 ENVELOPE PROTEIN GP 120

RELATIONSHIP TO OTHER APPLICATIONS

This application claims the benefit of and priority to U.S. Ser. No. 62/200,014 filed 1 Aug. 2015 and titled Polypeptide Glycopeptide Fragments from the V1/V2 and V3 Domains of the HIV-1 Envelope Protein gp120.

GOVERNMENT SUPPORT CLAUSE

This invention was made with government support under the following contracts. The government has certain rights in the invention. The following grants have been used to support this research.

NIDA Thai R01 DA 26801-01A1/SC#20090587; NIAID NIH Glycan R56 R56 AI 106556-01A1/SC#20130545; NIAID Glycan R01R01 AI 113893-01/SC#20140447.

FIELD OF THE INVENTION

Compositions and methods for treating or preventing HIV diseases.

BACKGROUND

A major goal in HIV vaccine research is the identification of antigens able to elicit the production of broadly neutralizing antibodies (bNAbs) effective against primary isolates of HIV. The applicant has investigated the molecular features of the HIV-1 envelope glycoproteins, gp160, gp120 and gp41, that confer sensitivity of viruses to neutralization.

BRIEF DESCRIPTION

Before this disclosure it was generally believed that that you need trimeric envelope proteins (e.g., gp140 trimers) to bind most broadly neutralizing antibodies directed to glycan dependent epitopes on gp120 (e.g. PG9, PGT121, PGT128 families).

PG9 is the prototypic bNAb that recognizes a mannose-5 dependent epitope in the V2 domain of gp120. This antibody is able to neutralize approximately 80% of virus isolates and is able to bind monomeric gp120, provided that the proper glycans are present (16-19). A vaccine that consistently elicits PG9-like antibodies would represent a significant improvement over the candidate HIV vaccines described to date.

The inventors have discovered that the glycosylation is different on trimeric proteins compared to monomeric proteins, and that monomeric scaffolds such as the ones described here, as well as those described in our previous patent and publication (Morales et al.) bind these broadly neutralizing antibodies if the glycosylation is correct, despite being monomeric or dimeric and not being trimeric in structure.

The inventors also disclose some new gp120 sequences that bind many broadly neutralizing antibodies directed to glycan dependent epitopes on gp120 (e.g. PG9, PGT121, PGT128 families). Some of these new gp120 sequences are particularly interesting because they bind the PGT121 and PGT128 families of antibodies when expressed in normal cells suitable for pharmaceutical production.

The inventors wish to point out that the present invention differs from that disclosed by Yang et al (J. Virology, 2004, 78(8):4029-4036) which does not disclose the specific glycan structures required to create a scaffold able to bind broadly neutralizing antibodies. The scaffolds described by Yang are short and do not have the glycosylation sites at N332 and N334 required for the binding of the prototypic PGT128 and other bNAbs.

V1/V2/V3 Domain Scaffolds

In brief, the V1/V2 domain was fused directly to the V3 domain to create a V1/V2/V3 domain scaffold that would bind broadly neutralizing antibodies.

The key insight underlying this invention is that Trimeric gp140 is not required to bind BNAbs, it is not the tertiary or quaternary structure per se that is key but it is the glycosylation of the structures that is important. The right glycosylation is critical, trimerization is not.

The fact is that the trimers have the right kind of glycosylation compared to the monomers makes them immunogenic, but the trimmers have many of "decoy" epitopes that make the trimmer effectively useless for vaccine purposes.

The hypothesis upon which the invention was based was that moving the N-terminal Glycosylation site from N334 (UCSC912) to N332 (UCSC1207) may allow scaffolds to bind the PGT121 family of bN-mAbs.

Two polypeptide scaffold sequences (#912 and #913) were created by the addition of an extra disulfide between the V3 crown and the addition of a connecting peptide between the B and C strands of the V1/V2 domain.

The initial two scaffolds (UCSC 912 and UCSC 913) differed by the addition of an extra disulfide (UCSC913) between the V3 crown and the connecting peptide between the B and C strands of the V1/V2 domain.

Polypeptide sequence 1209 and 1207 provided structures in which a glycosylation site in the scaffolds has been moved from position 334 to position 332.

V1/V2/V3 scaffolds were constructed by deletion of C1, C2, C3, V4, V5, and C5 domains and insertion of a signal sequence, purification tag, and flexible linker to induce broadly neutralizing antibodies. For the Thailand clade the embodiment would include the N334 sequence version, but for the African clade the 332 sequence would be used in the embodiment.

V1/V2 scaffolds.

The main embodiments above all concern constructs in which the V1/V2 domain was fused directly to the V3 domain to create a V1/V2/V3 domain scaffold. However, additionally, the inventors also disclose novel V1/V2 scaffolds without V3. The inventors have used HIV-1 sequence analysis with protein engineering to develop V1/V2 scaffolds able to bind PG9 when expressed in normal cell lines suitable for vaccine manufacturing. Disclosed are V1/V2 fragments from strains unable to bind PG9 that can be engineered to bind this antibody through a combination of point mutations in the β-hairpin formed by the B and C strands of the four stranded V1/V2 beta-sheet structure. These studies suggest that stabilizing the hydrophobic interactions in the hairpin structure is associated with improved stability of the PG9 binding epitope. More importantly, described is a novel V1/V2 scaffold from clade C virus can be engineered to bind PG9 with high affinity and can be produced in normal cell lines amenable for large scale cGMP vaccine production.

BRIEF DESCRIPTION OF THE FIGURES

FIG. 3A depicts sequences of scaffolds from HXB2 (SEQ ID NO:5), 108060 (SEQ ID NO:6), 108060 eng1 (SEQ ID NO:7), 108060 eng2 (SEQ ID NO:8), JRFL-E168K (SEQ ID NO:9), MN (SEQ ID NO:10), Bal.01 (SEQ ID NO:11), CAP.45 (SEQ ID NO:12), ZM197 (SEQ ID NO:13), ZM109 (SEQ ID NO:14), A244 (SEQ ID NO:15), A244.eng1 (SEQ ID NO:16), ZM233 (SEQ ID NO:17), ZM233.eng1 (SEQ ID NO:18).

FIG. 4 A. A244 V1/V2 Wildtype (GnTI-).

FIG. 4 B. A244 V1/V2 engineered (293F).

FIG. 4 C. ZM233 V1/V2 engineered (293F).

FIG. 5. (also referred to as Table S1). Listing of amino acid sequence and clade of wildtype and engineered V1/V2 scaffolds used for PG9 binding studies. FIG. 5 depicts sequences from 108060 (SEQ ID NO:19), MN (SEQ ID NO:20), JRFL-E168K (SEQ ID NO:21), A244 (SEQ ID NO:22), ZM233 (SEQ ID NO:23), Bal.01 (SEQ ID NO:24), CAP.45 (SEQ ID NO:25), ZM109 (SEQ ID NO:26), ZM197 (SEQ ID NO:27), 108060.eng1 (SEQ ID NO:28), 108060.eng2 (SEQ ID NO:29), MN.eng1 (SEQ ID NO:30), JRFL-E168K.eng1 (SEQ ID NO:31), A244.eng1 (SEQ ID NO:32), ZM233.eng1 (SEQ ID NO:33).

FIG. 6. (also referred to as Table S2). Summary of EC50s for PG9 binding to wildtype and engineered V1/V2 scaffolds determined by ELISA.

FIG. 7. (also referred to as FIG. S1). Binding of PG9 to additional wildtype V1/V2 scaffolds produced in normal and GnTI- 293 HEK cells as measured by ELISA. The scaffolds shown were not selected for additional protein engineering or PG9 binding studies.

FIG. 8. (also referred to as FIG. S2). SDS-PAGE analysis of V1/V2 scaffolds used for PG9 binding studies. Scaffolds from the A244, ZM233, MN, and 108060 isolates of HIV were expressed in either normal or GnTI- 293 HEK cells and purified by immunoaffinity chromatography followed by size exclusion chromatography. Samples of the recovered proteins were suspended in SDS-PAGE sample buffer with (R) or without (NR) added reducing agent. The proteins were then fractionated on 4-12% SDS PAGE gels (Invitrogen, Carlsbad, Calif.) and stained with SimplyBlue SafeStain (Life Technologies, Carlsbad, Calif.). Panels A-C indicate wildtype or engineered V1/V2 scaffold from the A244 isolate of HIV produced in either normal or GnTI- 293 cells as indicated. Panels D-F indicate engineered V1/V2 scaffolds from the ZM233, MN, and 108060 isolates expressed in normal 293 HEK cells. The proteins in panels A, C, and D were used to measure PG9 binding by surface plasmon resonance (FIG. 4).

FIG. 9. Two scaffolds UCSC912 and UCSC913. The sequence of UCSC912 is set forth in SEQ ID NO:34. The sequence of UCSC913 is set forth in SEQ ID NO:35.

FIG. 10. PGT 128 binding to scaffolds Absorbance vs. micrograms per ml. Pgt 128 binds to 1209 scaffolds grown in Kifunensine but does not bind to scaffolds grown in GNTI cells.

FIG. 11. PG9 binding graph Absorbance vs. micrograms per ml.

FIG. 12 Coating controls Absorbance vs. micrograms per ml.

FIG. 13 Summary of V1/V2/V3/C3 scaffolds without engineered disulfide bridges binding to bn-Mabs FIG. 14 V1/V2 domain was fused directly to the V3 domain to create a V1/V2/V3 domain scaffold.

DETAILED DESCRIPTION

Figure 1:
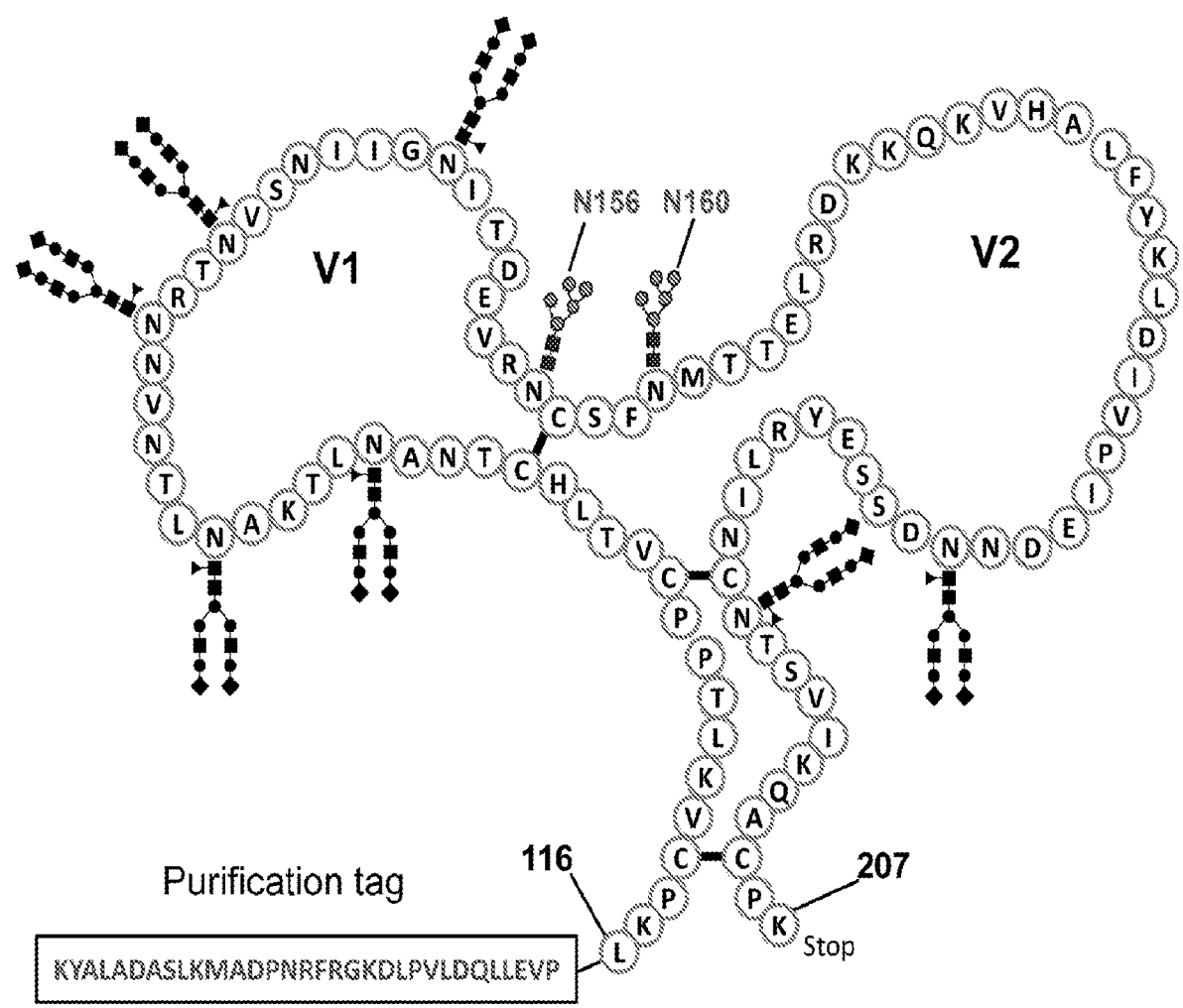
FIG. 1 Diagram of the V1/V2 scaffolds. The sequence depicted in FIG. 1 is set forth in SEQ ID NO:4.

The present disclosure describes the development of novel glycopeptide structures and fragments, exemplified by two specific novel glycopeptide fragments derived from the V1/V2 and V3 domains of the HIV-1 envelope protein gp120 for use as a component of a vaccine designed to elicit antibodies for the prevention and/or treatment of HIV infection.

The two novel glycopeptide fragments are as follows:

```
                                         SEQ ID No. 1
>Sequence 912_trimmed
ATGGGCGGAGCCGCCGCTAGACTGGGAGCCGTGATTCTGTTCGTCGTGAT

CGTGGGCCTGCATGGCGTGCGGGGCAAATATGCCCTGGCCGATGCCAGCC

TGAAGATGGCCGACCCCAACCGGTTCAGAGGCAAGGACCTGCCCGTGCTG

GATCAGCTGCTGGAGGTACCACTGAAGCCCGCCGTGAAGCTGACCCCTCC

TTGTGTGACCCTGCACTGCACCAACGCCAACCTGACCAAGGCCAATCTGA

CAAACGTGAACAACCGGACCAACGTGTCCAACATCATCGGCAACATCACC

GACGAAGTGCGGAACTGCAGCTTCAACATGACCACCGAGCTGCGGGACAA

GAAACAGAAGGTGCACGCCCTGTTCTACAAGCTGGACATCGTGCCCATCG

AGGACAACAACGACAGCAGCGAGTACCGGCTGATCAACTGCAACACCAGC

GTGATCAAGCAGGCCGCTCCCAAGATCAGCTTCGACCCTGGCGGCGGAGG

ATCTGGCGGAGGCGGAAGTGGCGGAGGGGGCTCTGTGATCAATTGCACCC

GGCCCAGCAACAACACCAGAACCAGCATCACCATCGGCCCAGGCCAGGTG

TTCTACCGGACCGGCGATATCATCGGAGACATCCGGAAGGCCTACTGCGA

GATCAACGGCACCGAGTGGAACTGA

SEQ ID No. 2
>Sequence 913_trimmed
ATGGGCGGAGCCGCCGCTAGACTGGGAGCCGTGATTCTGTTCGTCGTGAT

CGTGGGCCTGCATGGCGTGCGGGGCAAATATGCCCTGGCCGATGCCAGCC

TGAAGATGGCCGACCCCAACCGGTTCAGAGGCAAGGACCTGCCCGTGCTG

GATCAGCTGCTGGAGGTACCACTGAAGCCCGCCGTGAAGCTGACCCCTCC

TTGTGTGACCCTGCACTGCACCAACGCCAACCTGACCAAGGCCAATCTGA

CAAACGTGAACAACCGGACCAACGTGTCCAACATCATCGGCAACATCACC

GACGAAGTGCGGAACTGCAGCTTCAACATGACCTGCGAGCTGCGGGACAA

GAAACAGAAGGTGCACGCCCTGTTCTACAAGCTGGACATCGTGCCCATCG

AGGACAACAACGACAGCAGCGAGTACCGGCTGATCAACTGCAACACCAGC

GTGATCAAGCAGGCCGCTCCCAAGATCAGCTTCGACCCTGGCGGCGGAGG

ATCTGGCGGAGGCGGAAGTGGCGGAGGGGGCTCTGTGATCAATTGCACCC

GGCCCAGCAACAACACCAGAACCAGCATCACCTGTGGCCCAGGCCAGGTG

TTCTACCGGACCGGCGATATCATCGGAGACATCCGGAAGGCCTACTGCGA

GATCAACGGCACCGAGTGGAACTGA
```

Sequence 912 (SEQ ID No. 1) and sequence 913 (SEQ ID No. 2) as disclosed herein are glycopeptide fragments derived from the V1/V2 and V3 domains of the HIV-1 envelope protein gp120 and appear to be novel, and may be particularly useful as components of a vaccine designed to elicit antibodies for the prevention and/or treatment of HIV infection. A key feature of these fragments is that it they restrict antibody responses to the few epitopes in gp120 recognized by protective antibodies.

The two closest related sequences that the applicant has found are as follows: of WO2014043220 (Berman et al) SEQ ID No. 8; SQL 152; SCORE 298 65% of query selfscore 457 IDENT 97% BLASTALIGN; and WO2014043220 (Berman et al) PSL Disclosure; SEQ ID NO 8, SQL 152, SCORE 296 64% of query selfscore 461, IDENT 96% BLASTALIGN.

The glycopeptide fragments of the invention are folded in the proper conformation, and have the proper glycosylation (e.g. mannose-5 and/or mannose-9) required to bind the prototypic broadly neutralizing monoclonal antibodies, PG9 and PGT128, that recognize distinct glycan dependent epitopes in the V1/V2 and V3 domains of gp120, respectively. The glycopeptide fragments are not trimeric.

A key feature of these fragments is that they restrict antibody responses to the few epitopes in gp120 recognized by protective antibodies. Indeed, only a few of the scores of antibodies elicited by immunization with HIV envelope proteins have any protective effect. Moreover, the epitopes recognized by protective antibodies appear to be poorly immunogenic. By using a small fragment of the HIV envelope protein, containing at least two major epitopes recognized by broadly neutralizing antibodies, the applicant is able to selectively enhance the antibody response of these key sites and limit the immune response to the few regions of the molecule targeted by protective antibodies. The overall effect is to improve the potency of vaccines that include these epitopes compared to the potency that can be achieved by immunization with gp120 alone or with longer envelope constructs (gp140 or gp160).

A key inventive step in the development of these immunogens was the mutagenesis of gp120 to express only the V1/V2 and V3 domains in tandem, separated by a short flexible linker sequence.

To facilitate intracellular transport and secretion in mammalian cells, a signal sequence was fused to the amino terminus of the V1 domain.

To facilitate purification, a short flag epitope (N-terminal 27 amino acids from herpes simplex virus glycoprotein D or hexa-histidine tag) was inserted either at the N-terminus between the signal sequence and the V1 domain, or at the C-terminus at the end of the V3 domain.

Thus these immunogens required the fusion of at least 6 different DNA sequence elements including: 1) a signal sequence, 2) a purification tag, 3) the V1/V2 domain of gp120, 4) a flexible linker sequence, 5) the V3 domain of gp120, and 6) a translational stop codon at the end of the V3 domain.

The preferred construct possesses at least two disulfide bonds in the V1/V2 domain and a single disulfide bond in the V3 domain. In other embodiments there may be at least two disulfide bonds in the V1/V2 domain, or may be at least three, at least four, at least five or at least six, or more than 6. There may be a single disulfide bond in the V3 domain, or there may be more for example at least two, at least 3 or at least 4 or at least 5.

Examination of the 3-D structure of the HIV-1 envelope protein (trimeric gp140) reveal that the V1/V2 domains were in close spatial proximity in the properly folded envelope protein, but widely separated in the linear sequence of gp120. Using this structure, the applicants reasoned that the V1/V2 domain and the V3 domain could be fused together by elimination of the C2 domain normally separating these domains, provided that critical disulfide bonds required for maintaining the secondary structure were maintained.

Based on these insights, two different scaffold constructs have been created: One where the original disulfide bonds in the V1/V2 and V3 domains were preserved and separated by a short flexible linker, and another closely related construct where an additional disulfide bond was engineered to cross-link the V1/V2 domain to residues in the V3 domain.

The inventors found that both of these fragments/scaffolds were secreted efficiently from 293 HEK cells and were able to bind the broadly neutralizing PG9 and PGT128 antibodies, provided the proper glycosylation was present. PG9 binds to the V1/V2 domain. PGT128 binds primarily to the V3/C3 (V3 stem) domain, and PGT121 and PGT122 binds to contacts in both the V1/V2 and V3 stem domains:

Because the broadly neutralizing PG9 antibody requires mannose-5 for binding whereas the broadly neutralizing PGT128 antibody requires mannose-9 for binding, it has not yet been possible to produce the scaffold in a single cell line that incorporates both types of glycosylation. However, the inventors discovered they could use a "mixed-batch" fermentation process to create a mixture of scaffolds with some containing the mannose-5 required for PG9 binding and some with mannose-9 required for PGT-128 binding. The mixed batch process involves initial production in GnTI– 293 cell lines, which limits the glycans to mannose-5 structures. However, after 2-3 days, a glycosylation inhibitor (kifunensine) is added to the culture that limits glycosylation to mannose-9 structures. Thus the protein produced in the first few days of culture possesses the mannose-5 structures required for PG9 binding, while the proteins produced after the kifunensine addition limits the glycosylation of the newly synthesized proteins to the mannose-9 glycans required for PGT128 binding. In various embodiments the first cell line may be any cell line that limits the glycans to mannose-5 structures and a glycosylation inhibitor need not be kifunensine but may be any glycosylation inhibitor.

The two different scaffolds (same amino acid sequences, but different glycosylation) were then co-purified using a flag epitope at the N-terminus that did not distinguish between the two types of glycans present. While it may be costly to use GnTI– 293 cells or kifunensine in a commercial manufacturing process, these studies demonstrate the proof of the mixed-batch culture concept for simultaneously producing immunogens with different glycan modifications.

Therefore, it was shown that both scaffolds bound PG9 when expressed in GnTI– cells, but not kifenensine treated 293 cells. Conversely both scaffolds bound PGT128 when expressed in kifunensine treated 293 cells but not GnTI– cells.

Other strategies such as engineering cells for conditional inhibition of the mannosidase I gene in any GnTI– cell line (e.g. with a small inhibitory RNA) could achieve the same result and could be used for commercial production. The inventors are in the process of developing GnTI– CHO cells that conditionally express an siRNA inhibitor of mannosidase for use in the mixed-batch production of the V1/V2 V3 scaffolds.

Embodiments

The present invention encompasses a number of embodiments including the following:

A vaccine immunogen construct comprising fusion of the V1/V2 and V3/C3 domain of the HIV-1 envelope protein gp120. The V1 and V2 domains are contiguous sequences within gp120 and the V3/C3 domains are also contiguous sequences within gp120. Between the V1/V2 and V3/C3 domains are approximately 90 amino acids of the C2 domain. Thus the fusion product comprises a fusion of the contiguous sequence from the V1/V2 domain with the V3/C3 domain contiguous sequence by deletion of the C2 domain.

In certain other embodiments the construct may comprise the entire contiguous V1/V2 domain and the entire V3 domain and short segments from the C1, C2, and C3 domains.

Critically important to the function of some of these constructs are the conserved glycosylation sites located at the beginning of the C2 domain (N197) and at the end of the C2 domain (N289 and N295) and at the beginning of the C3 domain (N332 for most strains, but N334 for viruses from Thailand clade CRF01-AE).

Viruses from clade CRF01-AE typically possess the N334 glycosylation site whereas viruses from other clades possess the N332 glycosylation site. Thus the wild type A244 V1/V2/V3 scaffold (UCSC912) could be included in vaccines targeted for regions of the world where CRF01-AE viruses are common (e.g. Thailand, China) whereas the mutated scaffold (UCSC1207) could be included in vaccines targeted to the rest of the world where other clades (e.g. A, C, and D) predominate.

SEQ ID No. 3
>Sequence UCSC_1207:
MGGAAARLGAVILFVVIVGLHGVRGKYALADASLKMADPNRFRGICDLPV

LDQLLEVPLKPAVKLTPPCVTLHCTNANLTKANLTNVNNRTNVSNIIGNI

TDEVRNCSFNMTCELRDKKQKVHALFYKLDIVPIEDNNDSSEYRLINCNT

SVIKQAAPKISFDPGGGGSGGGGSGGGGSVINCTRPSNNTRTSITCGPGQ

VFYRTGDIIGDIRKAYC<u>NIS</u>GTEWN*

Certain embodiments specifically exclude a flag epitope such as gD-1, for example fragments that included the V2, V3, and C4 domain expressed without a flag epitope. Others specifically are expressed with a flag epitope such as gD-1.

Another embodiment encompasses a vaccine immunogen comprising polypeptide sequences specifically including (or derived from) the fusion of the V1/V2 and V3/C3 domain of the HIV-1 envelope protein gp120 containing N-linked glycosylation sites at positions 156, 160, N301 and N334 present in the 913 and 914 V1/V2/V3/C3 scaffolds.

Another embodiment encompasses a vaccine immunogen comprising sequences derived from fusion of the V1/V2 and V3/C3 domain of the HIV-1 envelope protein gp120 containing N-linked glycosylation sites at positions 156, 160, N301 and N332. Examples include the 1207 and 1209 V1/V2/V3/C3 scaffolds.

In all these examples the key feature is that the glycosylation sites must possess the right type of glycans, which is mannose 5 for the V1/V2 domain and mannose 9 for the V3 domain.

However, there are some exceptions. For example, the ZM233 V2 scaffold binds the broadly neutralizing PG9 and possesses only N160, and it has a structure that does not require the N156 glycan for antibody binding. Also, viruses from South and East Asia (clade CRF01-AE) lack the N332 glycan and instead possess the N334 glycan.

A further embodiment encompasses a vaccine immunogen comprising sequences of fusion constructs of the V1/V2 and V3/C3 domain of the HIV-1 envelope protein gp120 containing N-linked glycosylation sites at positions 160, N301 and N332. For example, envelope proteins derived from some viruses such as ZM233 that bind to PG9 despite the lack of the N156 glycosylation site.

A further embodiment encompasses a vaccine immunogen consisting of sequences derived from fusion of the V1/V2 and V3/C3 domain of the HIV-1 envelope protein gp120 containing N-linked glycosylation sites at positions 156, 160, N301 and N334 as in the 913 and 914 V1/V2/V3/C3 scaffolds.

In another embodiment the inventors disclose the engineered sequences in Tables S1 and S2 (FIGS. 5 and 6) that show good binding to the broadly neutralizing PG9 monoclonal antibody. These are sequences of the V1/V2 coding region alone and were expressed with various N-terminal signals sequences and flag epitopes. For this purpose, we most often used the signal sequence and flag epitope from HSV gD. However, we have also expressed these sequences with N and/or C terminal His tags. The gD flag allows purification over an affinity column made with an anti-gD monoclonal antibody. However, purification by this method entails a low pH elution step that has the potential to denature the scaffold. Using the hexahistidine tag allows for an affinity purification step under non-denaturing conditions. Low pH purification works for the V1/V2 scaffolds. These scaffolds have 3 disulfide bonds whereas other scaffolds may have only had two disulfide bonds. The inventors believe that two disulfide bonds is preferable but we also disclose V1/V2 scaffolds with 3 disulfide bonds which should be functionally equivalent.

Further Alternative Embodiments Encompass the Following

A vaccine immunogen consisting of sequences derived from fusion of the V1/V2 and V3/C3 domain of the HIV-1 envelope protein gp120 containing N-linked glycosylation sites at positions 156, 160, N301 and N332 as in the 1207 and 1209 V1/V2/V3/C3 scaffolds.

A vaccine immunogen consisting of sequences derived from fusion of the V1/V2 and V3/C3 domain of the HIV-1 envelope protein gp120 containing N-linked glycosylation sites at positions 160, N301 and N332 as in envelope proteins derived from some viruses (e.g. ZM233) able to bind PG9 despite the lack of the N156 glycosylation site.

A vaccine immunogen consisting of sequences derived from fusion of the V1/V2 and V3/C3 domain of the HIV-1 envelope protein gp120 expressed as a fusion protein in mammalian cells where a signal sequence is fused to the N-terminus and a flag epitope (e.g. His tag or sequences from another virus such as herpes virus glycoprotein D from humans or fruit bats) is incorporated at the mature N-terminus or C-terminus of the scaffold protein.

A vaccine immunogen consisting of sequences derived from fusion of the V1/V2 and V3/C3 domain of the HIV-1 envelope protein gp120 expressed as a fusion protein in mammalian cells where a signal sequence is fused to the N-terminus and a flag epitope (e.g. His tag or sequences from another virus such as herpes virus glycoprotein D from humans or fruit bats) is incorporated at the mature N-terminus or C-terminus of the scaffold protein and the protein is expressed in a cell line lacking the N acetyl-glucosaminyl transferase I gene and the mannosidase I gene is either silenced by an sHRNA or inhibited by a glycosylation inhibitor such as kifunensine.

A method of immunization where both primary and booster immunizations consist of the V1/V2/V3/C3 scaffold formulated in a non-toxic immunostimulatory adjuvant (e.g. alum, MF59, lipid A, GC rich synthetic DNA sequences) or any sequences capable of stimulating antibody responses.

A method of immunization where the primary immunization consists of monomeric gp120 or trimeric gp140 possessing the glycans required for the binding of broadly neutralizing antibodies from the PG9, PGT121, and PGT128 families and booster immunizations consist of the V1/V2/V3/C3 scaffold. Both immunogens are formulated in a non-toxic immunostimulatory adjuvant (e.g. alum, MF59, lipid A, GC rich synthetic DNA sequences) or any sequences capable of stimulating antibody responses.

A V1/V2/V3/C3 scaffold prepared from the clade CRF01-AE, A244 isolate of HIV-1.

A V1/V2/V3/C3 scaffold prepared from the clade B sequences 1201, 1202, 940F or 941 expressed in mammalian cells as described above with mannose-5 and mannose 9 glycans required to for binding broadly neutralizing monoclonal antibodies.

A V1/V2/V3/C3 scaffold prepared from the clade C sequences expressed in mammalian cells as described above with mannose-5 and mannose 9 glycans required to for binding broadly neutralizing monoclonal antibodies.

A plasmid or recombinant virus vaccine vector (e.g. adenovirus, pox virus, adeno-associated virus, or cytomegalovirus) containing sequences from the V1/V2/V3/C3 domains designed to express the scaffold when injected or transfected into humans (DNA vaccine).

Methods

Method for the production of cell lines useful for the expression of recombinant proteins that require mannose-5 and/or mannose 9 glycans for immunological activity are as follows.

Conditional Expression of shRNA to Inhibit Mannosidase 1 Expression in Human and Chinese Hamster Cell Lines to Produce HIV Vaccine Antigens with Mannose-9 Glycans.

A transcription unit directing the expression of an shRNA to inhibit mannosidase 1 (ManI) expression is inserted into a shuttle vector plasmid containing a bacterial origin of replication, a mammalian cell origin of replication, a selectable marker (e.g. amplicillin resistance) for plasmid replication in bacteria. A selectable marker for mammalian cell expression (e.g. dihydrofolate reductase or glutamine synthetase) can be included in the same plasmid or added in trans during mammalian cell line production.

Mixed Batch Production to produce a mixture of scaffolds with either mannose-9 or mannose-5 glycans from a single fermentation. 293 or CHO cells with a mutation in N-acetylglucosaminyltransferase I (GnTI−) are transfected with a plasmid with inducible U6 promoter repressing ER Man I shRNA. The transcription unit for an shRNA is constructed and functions as follows: The Tet repressor (TetR) is constitutively expressed under a strong mammalian enhancer/promoter (CMV or SV40). TetR binds the Tet operator sequence (TetO) within a U6 RNA polymerase III promoter sequence, preventing transcription of downstream ER ManI shRNA sequences. Upon the addition of tetracycline, TetR is released from TetO, allowing transcription by RN polymerase III of ER ManI shRNA to proceed. RNA polymerase III transcription encourages the formation of a double stranded RNA structure with a sense-loop-antisense motif. The sense strand is designed to be complementary to the mRNA of the gene intended to be silenced. The double stranded RNA is processed into pre-shRNA by Drosha before being exported to the cytoplasm. The pre-shRNAs are then cleaved by Dicer (dsRNA specific RNAse III enzyme), creating 19-25 nt double stranded siRNAs (silencing RNA) with overhangs at each end. The siRNA strands are then loaded into the RNA induce silencing complex (RISC) with Argonaute-2. Argonaute-2 unwinds the dsRNA to create a primed RISC capable of targeting specific mRNAs using the complementary shRNA fragments. Upon binding RISC degrades the target mRNA, effectively silencing the gene. With the expression of ER ManI inhibited, subsequent glycoprotein production will be limited to Man9 glycoforms. The siRNA strands are then loaded into the RNA induced silencing complex (RISC) with Argonaute-2. Argonaute-2 unwinds the dsRNA to create a primed RISC capable of targeting specific mRNAs using the complementary shRNA fragments. Upon binding RISC degrades the target mRNA, effectively silencing the gene. With the expression of ER ManI inhibited. Glycoprotein production may be limited to Man9 glycoforms.

According to the present disclosure, a mutation of A244 V1/V2/V3 scaffold moves N-terminal glycosylation site from N334 to N332 and improves binding of broadly neutralizing antibodies.

A244-rgp120 is able to bind bN-mabs from the PG9, PGT145, PGT125 and PGT135 families, but not the PGT121 family when grown in GNTi− cells.

A244-rgp120 bound 9 of the 11 bN-mAbs tested and the binding profile of A244-rgp120 is the same in GNTI− cells and kifunensine treated cells.

The 912 scaffold binds bN-mAbs only from the PG9 family when grown in GnTI− cells, but binds mAbs from the PG9 and PGT125 family when grown in kifunensine treated cells.

Mutation of the 912 scaffold to move the PNGS from N334 to N332 (1207 scaffold) confers the ability to bind the PGT121 and 122 bN-mAbs when grown in GnTI− cells.

Mutation of the 912 scaffold to move the PNGS from N334 to N332 (1207 scaffold) confers the ability to bind the PGT121 and 122 bN-mAbs when grown in kifunensine treated cells.

The 1207 scaffold grown in kifunensine binds 8/10 bN-mAbs tested. Mixed batch culture of the 1207 scaffold should bind 9/11 bN-mAbs in the panel tested.

Discussion

Glycopeptide scaffolds consisting of sequences from the V1/V2 and V3/C3 domain (including the V3 stem in the C3 domain) have been proved to be able to bind three major families of broadly neutralizing antibodies (PG9, PGT121, and PGT128) provided they are expressed with the proper glycosylation. These scaffolds provide the basis of a novel HIV-1 vaccine immunogens designed to stimulate antibody responses to the epitopes recognized by these antibodies when injected with a suitable adjuvant formulation.

This invention represents a significant improvement over previous vaccine based on monomeric or trimeric forms of the envelope proteins (gp120, gp140, or gp160) because it lacks the highly immunogenic epitopes that stimulate the formation of non-neutralizing antibodies. It is thought that these antibodies that bind to glycan independent sequences represent decoy epitopes that divert the immune response away from the glycan dependent epitopes recognized by broadly neutralizing antibodies.

The inventors also have developed and disclose a manufacturing process, call mixed batch fermentation whereby scaffolds with two different types of glycosylation can be produced in the same fermentation process. This eliminates the need for two different fermentations in order to produced scaffolds with mannose-5 and mannose-9 glycans.

The inventors have also invented a method to circumvent the need for the glycosylation inhibitor, kifunensine, in the production of scaffolds that incorporate mannose 9 glycans.

The inventors have also invented a method to circumvent the need for the costly glycosylation inhibitor, kifunensine, in the large scale production of scaffolds that incorporate mannose 9 glycans. The method makes use of a novel cell line (e.g. CHO, 293, or BHK) where the N-aceytlglucosaminyl transferase gene is inactivated by the CRISPER/CAS9 gene inactivation system to produce cell line that express only mannose 5 glycans. This cell line is further modified by transfection of a plasmid expressing of an shRNA able to silence the expression of the mannosidase I gene. For this purpose the shRNA gene is incorporated into a transcription unit with an inducible (tet) promoter. Thus the mannosidase I shRNA is tightly controlled by the tet repressor and only expressed when tetracycline is added to the cell culture medium. This system provides a practical, economic, and scalable alternative to the GnTI– 293 cells/kifunensine mixed batch culture system used to produce the V1/V2/V3 scaffolds with mannose 5 and mannose 9 glycans described herein.

The 912 scaffold should be effective in eliciting neutralizing antibodies specific for the PG9 epitope and the PGT128 epitope on CRF01-AE viruses that possess the N334 glycosylation site.

The 1207 scaffold should be effective in eliciting neutralizing antibodies specific for the PG9, PGT121 and 122 bN-mAbs when grown in GnTI– cells and PGT128 when expressed in kifunensine treated cells. Scaffolds of this type should be effective against viruses from all clades of HIV-1 except those from the CRF01-AE clade that possess the N334 glycosylation site.

Disclosure of V1/V2 (without V3) Scaffolds

The main embodiments above all concern constructs in which the V1/V2 domain was fused directly to the V3 domain to create a V1/V2/V3 domain scaffold. However, additionally, the inventors also disclose novel V1/V2 scaffolds without V3. The inventors have used HIV-1 sequence analysis with protein engineering to develop V1/V2 scaffolds able to bind PG9 when expressed in normal cell lines suitable for vaccine manufacturing. The V1/V2 scaffolds are discussed below.

The inventors have combined HIV-1 sequence analysis with protein engineering to develop V1/V2 scaffolds V1/V2 scaffolds able to bind PG9 when expressed in normal cell lines suitable for vaccine manufacturing. The inventors show V1/V2 fragments from strains unable to bind PG9 could be engineered to bind this antibody through a combination of point mutations in the β-hairpin formed by the B and C strands of the four stranded V1/V2 beta-sheet structure. The studies suggest that stabilizing the hydrophobic interactions in the hairpin structure is associated with improved stability of the PG9 binding epitope. More importantly, the inventors describe a novel V1/V2 scaffold from clade C virus can be engineered to bind PG9 with high affinity and can be produced in normal cell lines amenable for large scale cGMP vaccine production.

Results: PG9 binding to V1/V2 scaffolds from multiple clades Scaffolds consisting of the V1/V2 domains of viral Clades B, C, and E were constructed and screened for binding of PG9, a prototypic bNAb targeting a GDE in the V1/V2 domain. Since previous studies have shown that PG9 requires mannose-5 at N156 and N160, scaffolds were expressed in normal 293F cells and 293-GnT1– cells. Cells were transfected with genes encoding the V1/V2 scaffolds and the resulting glycopeptides were secreted into the cell culture supernatants were tested for PG9 binding by indirect ELISA. The inventors found FIG. 1, that PG9 bound 1 V1/V2 scaffolds from several strains of HIV-1. In particular, the best binding was observed for scaffolds from the A244, ZM109, and ZM233 isolates produced in GnT1– cells. Weak binding was observed for most of the scaffolds produced in normal 293F cells, however the inventors noted that scaffolds from the clade B viruses (MN and 108060) showed no binding to PG9. Surprisingly, the scaffold from the clade C, ZM233 isolate, showed moderate binding to PG9 even when produced in 293F cells. This isolate is particularly interesting because clade C viruses represent the clade of virus predicted to be responsible for the majority of new infections over the next decade (ref) and because it is one of the few envelopes that lack a glycosylation site at N156 that in some cases is important for PG9 binding (ref). In this strain, isoleucine (I) replaces asparagine (N) at position 156.

Amino Acid Alignment of V1/V2 Scaffolds

Sequence alignment of scaffolds able to bind PG9 with those unable to bind PG9 (FIG. 2) allowed us to identify elements within the V1/V2 region that influenced PG9 binding The V1/V2 domain is a glycan rich region (typically 9 N-liked glycosylation sites) that exhibits a high level of amino acid sequence diversity. Previous alignments of this regions have highlighted multiple polymorphisms in amino acid sequence including, replacements, insertions and deletions that alter the length of this region as well as the location and number of N-linked glycosylation sites. The variation in the V1/V2 domain is thought to represent an immune escape strategy that affects the exposure and immunogenicity of neutralizing epitopes through conformational masking and glycan shielding. The inventors next mapped amino acid differences between scaffolds that differed in their ability to bind PG9 mapped onto the crystal structure of the V1/V2 (McLellan et al, Julian, et al Lyumkis et al).

The crystal structure of the V1/V2 domain shows it adopts a four stranded antiparallel β-sheet consisting of the A, B, C, and D and the connecting peptides between individual strands. Strands B and C form a β-hairpin with a short turn region (Supplemental FIG. 6). 3-D structures of PG9 and PG9-like antibodies co-crystallized with the V1/V2 domain have shown that these antibodies interact with the hydrophilic side of the β-hairpin. Critical contacts are also made with glycans at N156 and N160 as well as basic amino acids at 168, 169, and 171. Recognizing that PG9 interacts with the hairpin the inventors focused on amino acid changes in this region that may stabilize and enhance the binding of this antibody. Previous studies with synthetic glycopeptides have shown that stabilizing the hairpin with disulfide bonds can improve antibody binding (e.g., to PG9) and neutralization. It is well-known that cross-strand interactions between sidechains and the turn region are important for hairpin formation and stability. Inspection of the structures allowed us to identify several amino acids from the alignment that seemed to be associated with stabilizing interactions and enhanced PG9 binding. Interestingly, many of these interactions do not appear to be contact sites required for antibody binding.

Effect of Amino Acid Mutations in the B and C Strands on PG9 Binding

The inventors next carried out experiments where mutations identified from the alignment and the structures were sequentially introduced into a clade B V1/V2 scaffold (108060) that did not bind PG9. This isolate contains many of the amino acids required for PG9 binding with the exception that it appeared to lack a critical contact at position 169 where isoleucine (I) replaces a critical a lysine (K). The inventors found that replacement of K for I at position 160 (I169K mutant) improved PG9 binding when expressed in GnT1– cells, but had no effect in 293F cells. Since K169 is known to be a required contact for PG9 binding, the I169K mutant became our template for further analysis.

The next mutation made was E172V. Valine was selected for several reasons. First, it is an amino acid frequently found in β-sheet structures. Valine, isoleucine, and threonine have a β-branched carbon that limits the conformations the main-chain backbone can adopt. Second, valine is a hydrophobic amino acid and can form cross-strand interactions with other hydrophobic amino acids on opposing strands. In the B-C hairpin, V172 is in the middle of strand C and could interact with F159 on strand B. Third, valine was found to be an important amino acid for antibodies that targeted the C-strand in RV144 vaccinated individuals. As shown in FIG. 3c, the combination of I169K/E172V significantly improved PG9 binding when expressed in GnT1$^{-1}$ cells but did not bind when expressed in 293F cells. Interestingly, position 172 is not a contact site for PG9; the amino acid is oriented on the opposite side of the PG9 contact surface. Therefore, V172 on the C strand might indirectly influence binding by enhancing the interaction with F159 on B strand. This, in turn, would be predicted to enhance hairpin formation and stability.

The I169K and E172V mutant of the 108060 scaffold became the new template to optimize antibody binding.

When a mutation, or a combination of mutations, showed an improvement in PG9 binding it was added and became the starting template for the next round of mutagenesis. The inventors next selected the T161M polymorphism found in the alignment for the next round of mutagenesis. The inventors found (FIG. 3d, that this mutant did improve binding when expressed in GnT1⁻ cells, but did show a slight improvement in 293F cells. Similar to E172V polymorphism, the T161M is oriented on the opposite side of the PG9 contact surface and does not interact directly with the antibody; the improvement in binding is indirect and cross-strand hydrophobic interactions between F159, 161M and V172 may alter hairpin formation and this may explain the difference in binding.

It is known that PG9 and PG9-like antibodies do not always require glycosylation at N156 for binding and neutralization. However, this has not been explored in the context of a V1/V2 scaffold. Based on the sequence alignment, and the observation that ZM233 has an Iat position 156 the inventors decided to remove the glycosylation site on our mutant 108060 V1/V2 scaffold and replace it with an isoleucine. As shown in FIG. 3e, the scaffold bound PG9. The inventors found that the loss of the glycan at N156 and substitution with isoleucine did not reduce PG9 binding. The isoleucine substitution showed a slight improvement in binding for both cell lines compared to the previous mutant. This was surprising because the crystal structure of V1/V2 domain from the CAP.45 isolate shows that PG9 makes considerable contacts with the glycan at N156.

Effect of Mutations in the B-C Turn on PG9 Binding

The B-C turn (residues 164 to 167) is the short segment connecting the B and C strands. The turn region has been shown to influence formation of β-hairpin. Statistical analysis of amino acids found in turns show a preference for small amino acids, such as glycine, and also a preference for proline, asparagine, and aspartate. Based on the alignment, several small amino acids in the B-C turn (e.g. positions 164 and 167) were identified as possibly being important for stabilizing this structure. Most viral sequences contain a glutamate (E) at 164 and aspartate (D) at 167, where E occupies the i position and D the i+3 position in the turn sequence. A hydrogen bond between the main chain carbonyl group from i and the amino group from i+3 helps stabilize the turn. However, the presence of two negatively charged amino acids at the i and i+3 positions may affect hairpin formation in the context of the V1/V2 scaffold. To investigate this 164 and 167 were mutated to glycine. Mutating these sites served several functions. First, glycine can adopt a wider range of Φ and ψ angles necessary for β-turns. Second, removing the negative amino acids occupying the i or i+3 positions may increase the turn propensity. Third, position 167 is a key site for the development of some PG9-like and strain-specific quaternary antibodies to the V2 domain. Glycines at 164 and 167 were added onto the 108060 mutant. As shown in FIG. 3f, these changes had a dramatic effect on PG9 binding. It can be seen that binding of PG9 increased.

To further investigate the role the turn has on PG9 binding, the inventors tested another turn sequence. This sequence was not identified from the alignment, but rather identified from the literature (ref) as a strong promoter of hairpin formation. The optimized turn was a proline-glycine combination. Proline is statistically preferred at the i position for many common turn types, and adding a proline introduces a kink into strand B that restricts the φ to −60. Proline was added at position 164 and glycine at position 165 on the 108060 mutant. The inventors found the proline-glycine mutations had a similar effect on PG9 binding as the glycine-glycine mutations. As shown in FIG. 4g, strong binding was seen in GnT1⁻ cells and moderate binding with 293F cells.

Incorporating the Mutations into Other Viral Strains

Next, the inventors next wanted to know if the mutations introduced in the 108060 V1/V2 scaffold would similarly be effective in V1/V2 scaffolds from other viral strains. V1/V2 scaffolds for MN and JRFL E168K were constructed and tested for PG9 binding. As shown in FIG. 4a-b, no binding was observed with the wild-type sequences. ZM233 V1/V2 scaffold was also included (FIG. 4c). Next, the inventors incorporated the amino acid changes to the B and C strands and turn that were effective in improving binding to the 108060 scaffold. Examination of the sequences from the clade B MN and JRFL E168K V1/V2 domains revealed that these proteins contained additional changes in the V1 domain. MN lacked glycosylation sites at N130 and N143 and possessed an 8 amino acid deletion in the V1 loop. JRFL E168K lacked glycosylation sites at N138 and N143. Previous work has suggested a shorter V1 domain with fewer glycosylation sites may change the exposure of the epitope for PG9 and other BNabs to the V1/V2 domain. Interestingly the ZM233 envelope protein has a short V1 domain and showed good binding when tested by ELISA. As shown in FIGS. 4d-f, the mutations added to MN, JRFL E168K, and ZM233 had a dramatic effect on PG9 binding. The most impressive change was seen for ZM233 (FIG. 5f). The ZM233 mutant produced in both GnT1⁻ and 293F cells had $EC_{50}$ values of 0.01 ug/ml and 0.002 ug/ml, respectively. Interestingly, ZM233 already contains many of the mutations identified from the alignment and only required changes to the turn region.

Endo H Treatment of V1/V2 Scaffolds

The binding of PG9 to gp120 normally depends on mannose-5 at N160 for binding. To determine if the V1/V2 mutants expressed in 293F cells still required glycosylation at N160 for binding the inventors treated the scaffolds with the glycosidase Endo H and observed their ability to bind PG9. Endo H cleaves high mannose and some hybrid N-linked oligosaccharides; it will not cleave complex oligosaccharides. If the V1/V2 mutants produced in 293F cells contain mannose-5 or other high mannose glycans at N160, Endo H will remove these and should inhibit PG9. If complex glycans are present at N160 they will be resistant to Endo H and be unable to bind PG9. The inventors found (FIG. 5a-d), that mock digested V1/V2 scaffolds bound PG9 whereas Endo H digested V1/V2 scaffolds (FIG. 5e-h) destroyed the PG9 binding activity. Therefore, it appeared that PG9 binding still depended on high mannose or hybrid oligosaccharide at N160 for binding.

Affinities of PG9 Binding to V1/V2 Scaffolds.

The inventors used surface plasmon resonance (SPR) to measure the binding affinity of PG9 to the mutant scaffolds expressed in 293F cells. For these measurements purified goat anti-human Fc antibodies were coated onto SPR detection chips and used to capture PG9. The V1/V2 scaffolds were then flowed over the chip at concentrations of 40 ug/ml, 30 ug/ml, 20 ug/ml, and 10 ug/ml. As shown in FIG. 6, the wildtype scaffolds for MN and 108060 showed no binding to PG9. The mutant scaffolds for MN and 108060 showed weak to moderate binding, with $K_D$ values of 118 nM and 74 nM, respectively. The ZM233 mutant showed relatively high binding affinity to PG9 with a $K_D$ of 33 nM. Interestingly, the ZM233 mutant has a much faster on-rate compared to the other V1/V2 scaffolds. This faster on rate may be due to the lack of the N156 glycosylation site, a more stable, hairpin structure or bett the inventors exposure of the PG9 epitope due to the short V1 domain.

Discussion

Here the inventors describe efforts to engineer fragments of the V1/V2 domain that enable the binding of the prototypic broadly neutralizing mAb PG9 when expressed in normal cell lines. Comparison of sequences that differed in the ability to bind PG9 revealed naturally occurring polymorphisms from viral sequences that affected binding. These mutations occurred in the 0-hairpin formed by the B and C strands. The inventors found mutations associated with improving hairpin formation and stability, that were independent of PG9 contact residues, were also associated with enhanced PG9 binding. In particular, hydrophobic amino acid changes in the B and C strands along with changes in the turn region had a dramatic effect on binding.

PG9 critically depends on mannose-5 at N160, but the amino acid and glycan occupying position 156 can vary. Previous work has shown PG9 can recognize both complex and hybrid type glycans at N156. Here the inventors show the glycan at N156 is not necessary for PG9 binding in the context of a V1/V2 scaffold. In fact, the V1/V2 mutant for 108060 showed a slight improvement in binding when N was mutated to I. This was surprising because the crystal structure of the CAP.45 V1/V2 domain showed that 27% of the contact surface for PG9 is made with the glycan at N156. This observation follows a pattern seen with other HIV BNab's. Particularly, the ability of some broadly neutralizing antibodies to recognize both high mannose and complex glycans, and the ability to recognize nearby glycans reveals how broadly neutralizing antibodies have evolved to form promiscuous interactions with adjacent glycans in closely related epitopes. PG9 binding may follow a similar strategy. This may explain why it can bind to V1/V2 scaffolds that lack N156 and can also bind when high mannose or complex glycans are present at this site. It appears mannose-5 at N160 is essential for PG9 binding, but position 156 can vary in both site occupancy and glycan type.

The ZM233 mutant scaffold produced in 293F cells showed high affinity binding when tested by surface plasmon resonance. The $K_D$ for PG9 binding to the scaffold was 33 nM. This is comparable to values obtained for disulfide stabilized synthetic glycopeptides containing mannose-5 at N156 and N160, and is also comparable to values the inventors have obtained for an A244 V1/V2 scaffold produced in GnT1- cells (unpublished data). While the affinity of PG9 to the V1/V2 scaffolds is not as high as trimeric gp140 from the BG505 strain of HIV-1 our data nevertheless shows high affinity binding is possible for a V1/V2 scaffold produced in 293F cells. Additionally, development of a vaccine based on the ZM233 V1/V2 mutant may be significant. The predicted germline gene for PG9 has been shown to neutralize ZM233 (ref). Several studies have recently suggested that immunogens capable of direct binding to the germline immunoglobulin genes of BNabs may represent a new class of be superior vaccine immunogens.

Several conclusions can be drawn from these studies. First, mutations in the B-C hairpin significantly improved PG9 binding for the viral strains tested even though many of the changes do not occur at antibody contact sites and may influence binding indirectly by altering hairpin formation. Second, antigenicity can be engineered for some V1/V2 scaffolds and many of the factors responsible for PG9 binding have been identified. However, variables such as V1 loop length, V2 loop length, or number of glycosylation sites may be equally important for exposing the PG9 epitope. Third, the ZM233 mutant scaffold showed high affinity binding when it was produced in normal 293F cells. Fourth, this is the first report of a V1/V2 scaffold showing high affinity binding when expressed in a normal cell line. Finally, the development of scaffolds able to bind PG9 with high affinity appears to require combinations of mutations rather than single point mutations. While some of these mutations can be discovered from comparative sequence analysis coupled to antibody binding studies, others were discovered by applying well-known rules of protein folding related to hairpins. The scaffolds created provide an approach to selectively stimulate and focus the antibody responses to an important glycan-dependent epitope in the V1/V2 domain without stimulating antibodies to other immunodominant regions of Env. Preliminary immunogenicity studies with V1/V2 scaffolds produced in GnT1- cells suggest that they can improve protective antibody responses compared to immunization with gp120 alone. However because human bNAbs such as PG9 have exceptionally long CDRH3 domains, it is unlikely that that the true immunogenic potential of V1/V2 scaffolds can be determined in animal immunogenicity studies alone. The development of scaffolds that can be produced in normal 293 and CHO cell lines, such as the such as the ZM233 scaffold described above, will allow for the cGMP production of V1/V2 scaffolds that can be tested in human immunogenicity studies.

Materials and Methods:

Construction of V1/V2 scaffolds—Bal.01 (ref); CAP45.2.00.G3, SVPC16 (ref); SC422661, Clone B SVPB8 (ref); ZM109F.PB4, SVPC13 (ref); ZM197M.PB7, SVPC6 (ref); ZM233M.PB6, SVPC9 (ref); were obtained from the NIH AIDS Reagent Program (Germantown, Md.). A244, 108060, MN, and JRFL E168K V1/V2 constructs have been previously described. (ref) gD tagged V1/V2 constructs contain the herpes simplex virus (HSV) signal sequence, an N-terminal HSV gD tag epitope for affinity purification, and V1/V2 domain. His6x-StrepTag constructs contain the ICAM signal sequence, a Hexa-histidine (His6x) tag and StrepTag for tandem affinity purification, and V1/V2 domain. The amino acid sequences for all V1/V2 scaffolds used in this study are provided in the supplement.

Production and purification of V1/V2 scaffolds—Plasmids were transfected into FreeStyle™ 293-F cells (Invitrogen, Carlsbad, Calif.) or into GnTI- 293 cells (293 cells deficient in N-acetylglucosaminyltransferase I; ATCC No. CRL-3022) that limit N-linked glycans to simple, mannose-5 containing glycan structures (American Type Culture Collection Manassas, Va.). Transfections were carried out with polyethyleneimine (PEI) and the supernatant was collected on day 3 or day 4. For gD-tagged constructs, immunoaffinity chromatography was used to purify the proteins as described previously (ref). To purify His6x-Streptag constructs, HisTrap and StrepTactin sepharose high performance columns (GE Healthcare Biosciences) were used for purification. Purified proteins were run on a _size exclusion column. All proteins were buffer exchanged into TBS. The resulting proteins were analyzed by SDS-PAGE using 4-12% precast gradient gels (Invitrogen).

Antibodies—PG9 and PG16 monoclonal antibodies were purchased from Polymun Scientific GmbH. (Vienna, Austria) 34.1 is a mouse monoclonal antibody specific for the N-terminal gD flag epitope of HSV-1 and was used as a capture antibody in indirect ELISA assays (Morales, J F et al., unpublished data). Mouse anti-His6x Mab was purchased from R&D systems—Clone# AD1.1.10. (Minneapolis, Minn.) Human IgG1 Isotype control Mab was purchased from Sigma-Aldrich. (St. Louis, Mo.)

Indirect ELISAs with cell supernatant—The following protocol was used to measure PG9 binding to V1/V2 scaffold from cell supernatant. Nunc Maxisorp ELISA plates (Nunc, Rochester, N.Y.) were coated with 2 μg/ml of 34.1 anti-gD antibody in PBS overnight at 4° C. The following day the plates were washed 4 times with PBS containing 0.05% Tween-20, and blocked for 2 hrs with PBS containing 1% BSA (blocking buffer). Cell supernatant containing V1/V2 scaffold from 3 days post-transfection was added at 100 ul/well. (Western blot was used to confirm scaffold expression.) Dilutions of PG9 or Isotype control was added from 10 g/ml to 0.001 ug/ml.

Peroxidase-conjugated AffiniPure Goat Anti-Human IgG, (Fcγ specific) (Jackson ImmunoResearch, West Grove, Pa.) was used at a 1:5000 dilutions. OPD substrate (Fisher Scientific, Pittsburgh, Pa.) was developed for 10 min and stopped with 3 M $H_2SO_4$. The absorbance was measured at 490 nm. All steps, except coating, were done at room temperature on a shaking platform; incubation steps were for 1 hr. All dilutions (except coating) were done in blocking buffer. Wash steps were included after incubation.

Indirect ELISAs with V1/V2 mutants—PG9 binding to V1/V2 mutant scaffolds was done by capture ELISA. Maxisorp microtiter plates (Nunc, Rochester, N.Y.) were coated with 2 μg/ml of the 34.1 anti-gD antibody in PBS overnight at 4° C. The plates were then washed 4 times with PBS containing 0.05% Tween-20, and blocked for 2 hrs with PBS containing 1% BSA (blocking buffer). Saturating amounts of recombinant gD-V1/V2 scaffold were added at 10 μg/ml. Serial dilutions of PG9 were added from 10 μg/ml to 0.001 ug/ml. Peroxidase-conjugated AffiniPure Goat Anti-Human IgG, (Fcγ specific) (Jackson ImmunoResearch, West Grove, Pa.) was used at a 1:5000 dilutions. OPD substrate (Fisher Scientific, Pittsburgh, Pa.) was developed for 10 min and stopped with 3 M $H_2SO_4$. The absorbance was measured at 490 nm. All steps, except coating, were done at room temperature on a plate shaker; incubation steps were for 1 hr (except blocking), and all dilutions were done in blocking buffer.

Endo H digests and ELISA—Endo H cloned from *Streptomyces picatus* and expressed in *E. coli* was purchased from New England Biolabs, (Boston, Mass.). Endo H cleaves high mannose and some hybrid N-linked oligosaccharides between the two N-acetylglucosamine residues in the diacetylchitobiose core. Endo H will not cleave complex glycans. V1/V2 scaffolds used in the Endo H assays were expressed in FreeStyle™ 293-F cells and were digested under native conditions. Briefly, 30 ug of V1/V2 scaffold in 50 mM sodium citrate buffer pH 5.5 (G5 buffer) was digested with 500 U of Endo H overnight at 37° C. Mock digestions were run under the same conditions with Endo H not included. Maxisorp ELISA plates were coated with 5 ug/ml of Endo H-digested V1/V2 scaffold overnight at 4° C. The following day, the plates were washed 4x with PBS+0.05% Tween-20 and blocked for 2 hrs using 1% BSA in PBS. PG9, IgG1 Isotype control, or anti-His6x were added at 10 ug/ml to 0.001 ug/ml. HRP-labeled anti-human IgG Fc or anti-mouse IgG Fc was added at 1/5000 dilution. OPD substrate was developed for 10 min. and stopped with 3M $H_2SO_4$. The absorbance was measured at 490 nm. All incubation steps (except blocking) were for 1 hr at room temperature on a plate shaker. All dilutions (except coating) were done with 1% BSA and PBS. Washes were included after incubation steps.

Surface plasmon resonance. Kinetic analysis of V1/V2 scaffold binding to PG9 was run on a Biacore 3000 instrument. Human antibody capture kit (GE Healthcare/Biacore) was used to immobilize anti-human IgG Fc to a CM5 sensor chip using primary amine chemistry. Briefly, the carboxymethylated dextran surface was activated using EDC/NHS, anti-human IgG Fc was conjugated to the chip, and the reaction blocked using 1M ethanolamine-HCl. HBS-EP was the running buffer and was also used for antibody dilutions. Isotype control and PG9 was captured to 50-100 RU. Five concentrations of V1/V2 scaffold were tested: Analysis was done with Biaevaluation software and fit to a 1:1 Langmuir model. Background was subtracted from the Isotype control.

Disclosure of V1/V2 (without V3) Scaffolds that Bind PG9

To further complete this disclosure, the inventors herein also disclose engineered V1/V2 scaffolds of HIV-1 gp120 that bind the glycan-dependent neutralizing antibody PG9 when produced in normal cells. Glycopeptide scaffolds from the V1/V2 domain of gp120 have been created for use in HIV vaccines to target antibody responses to glycan-dependent and glycan-independent epitopes recognized by antibodies thought to mediate protective immunity.

The V1/V2 domain of HIV-1 envelope protein gp120 contains epitopes recognized by antibodies important for protective immunity. However, the V1/V2 domain is poorly immunogenic, and expression of recombinant gp120 in cell lines suitable for biopharmaceutical production typically results in the incorporation of sialic acid-containing glycans that prevent the binding of glycan-dependent broadly neutralizing antibodies. In this report, we describe the development of glycopeptide scaffolds from the V1/V2 domain that bind the prototypic broadly neutralizing antibody PG9 with high affinity when expressed in normal cell lines. These scaffolds represent a solution to three current challenges in HIV development: the difficulty in manufacturing vaccine antigens that possess glycan-dependent epitopes required for the binding of broadly neutralizing antibodies; the poor immunogenicity of epitopes in the V1/V2 domain; and the immune-dominance of antibody responses to non-protective "decoy" epitopes in other parts of gp120.

PG9 is able to neutralize approximately 80% of virus isolates and is able to bind monomeric gp120, provided that the proper glycans are present (16-19). A vaccine that consistently elicits PG9-like antibodies would represent a significant improvement over the candidate HIV vaccines described to date. An important aspect of this effort was to develop scaffolds that could expressed in normal cell lines. Although monomeric gp120 and V1/V2 scaffolds with the proper glycosylation can be produced at analytical scale using costly glycosylation inhibitors or cell lines with glycosylation pathway enzyme mutations (e.g., GnTI– cells), these conditions are not practical for the large scale production of immunogens required for clinical trials. In this report we describe the development of V1/V2 scaffolds from three different clades of HIV that bind PG9 with high affinity and can be produced in cell lines of the type commonly used for production at the multi-gram scale required for human vaccine trials.

Results

PG9 Binding to V1/V2 Scaffolds from Multiple Clades.

Figure 2:
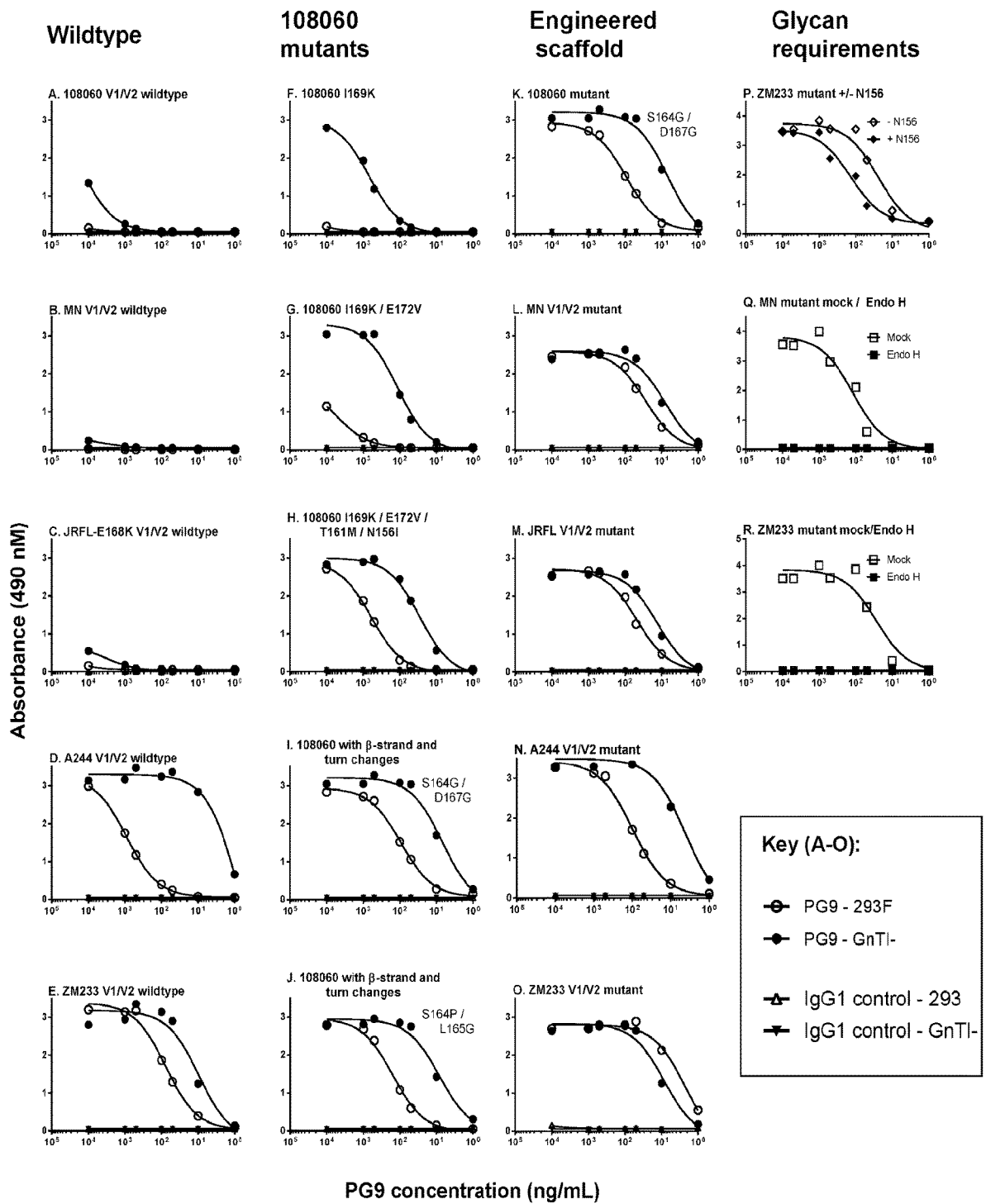
FIG. 2 Graphs of absorbance vs. PG9 concentration.

Genes encoding scaffolds from the V1/V2 domain, similar to those described previously (19, 25) were synthesized based on the sequences of envelope proteins from nine different viruses (FIG. 1, Table S1). These included viruses representative of those circulating in North America and Europe (clade B), Southern Africa and East Asia (clade C), and Southeast Asia (CRF01_AE). These were expressed by transient transfection in normal 293 HEK cells and in GnTI– 293 HEK cells that limit N-linked carbohydrate to mannose-5 glycans. Growth conditioned cell culture medium was harvested from these cells, and screened for PG9 binding by ELISA (FIG. 2, A-E; FIG. S2). Previous studies have reported that PG9 typically requires mannose-5 at positions N156 and N160 for binding (FIG. 1B), although some strains only require mannose-5 at N160 (16, 17). Normal cell lines used for protein expression such as 293 HEK and CHO typically incorporate a mixture of high mannose, hybrid, and complex, sialic acid-containing glycans (FIG. 1B). Of these, PG9 binding appears to have an absolute requirement for mannose-5 at position 160 (7, 17, 26). We found that PG9 bound V1/V2 scaffolds from six of the nine strains tested when grown in normal 293 cells and seven of nine proteins expressed in GnTI– cells. The highest PG9 binding affinities were observed with the A244 and ZM233 scaffolds that exhibited EC50s of 0.74 and 9.5 ng/ml when produced in GnTI– cells (FIGS. 2 D and E, Table S2). In all cases, binding to the proteins produced in normal cells was weaker than binding to proteins expressed in GnTI– cells. The scaffold best able to bind PG9 when expressed in normal 293 cells was derived from the ZM233 strain and bound with an EC50 of 77.1 ng/ml. Interestingly, the ZM233 scaffold lacked the N156 glycosylation site often required for PG9 binding in other strains (7, 16). Based on these observations, we selected five scaffolds with three different PG9 binding phenotypes for further study (FIG. 2, A-E). These included the 108060, MN, and JRFL-E168K scaffolds that showed poor binding to PG9 when expressed either in 293 or GnTI– cells; the A244 scaffold that gave poor binding when expressed in normal cells but high affinity binding when expressed in GnTI– cells; and the ZM233 scaffold that exhibited moderate and high affinity binding when expressed in either normal or GnTI– cells.

Amino Acid Alignment of V1/V2 Scaffolds

Figure 3:
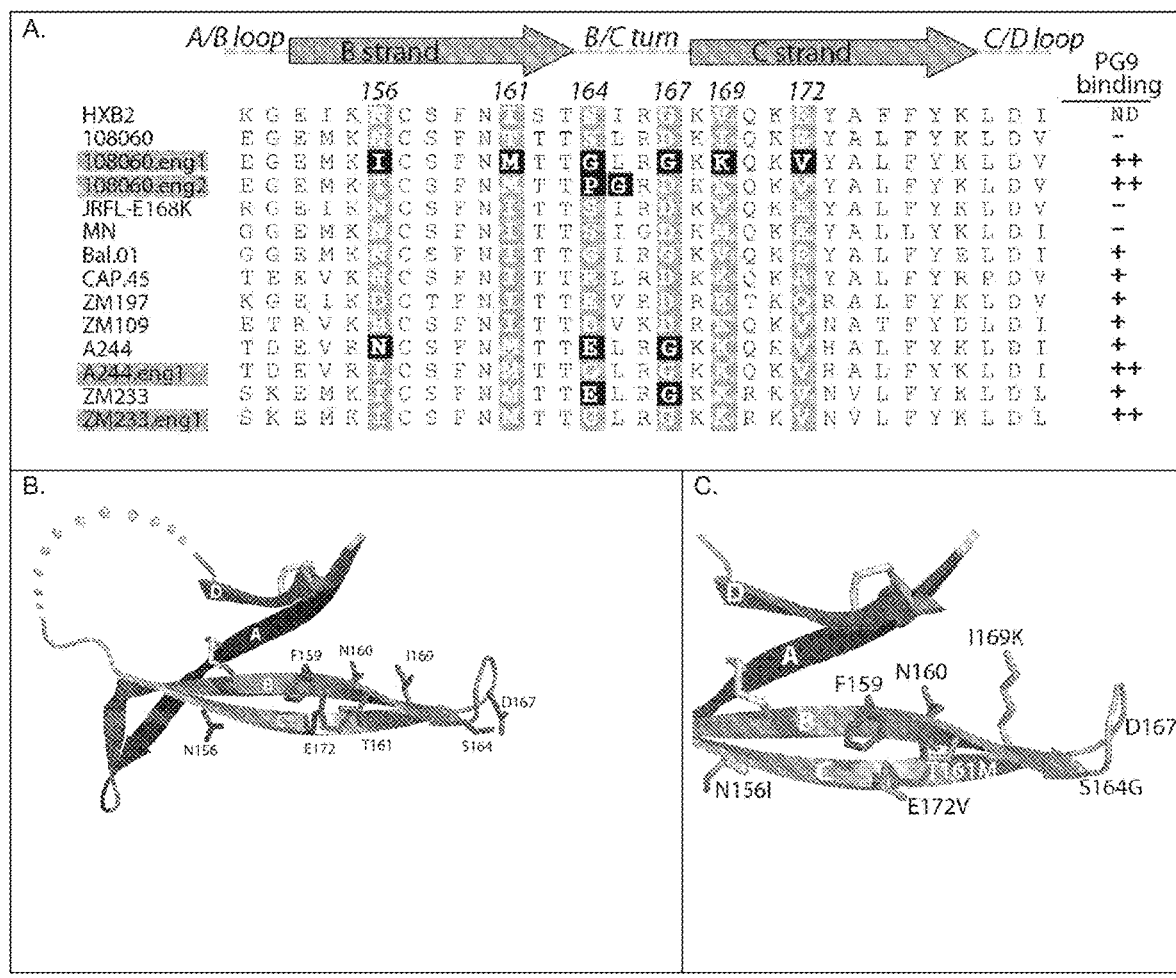
FIG. 3A-C Construct sequences and structures.
Figure 14:
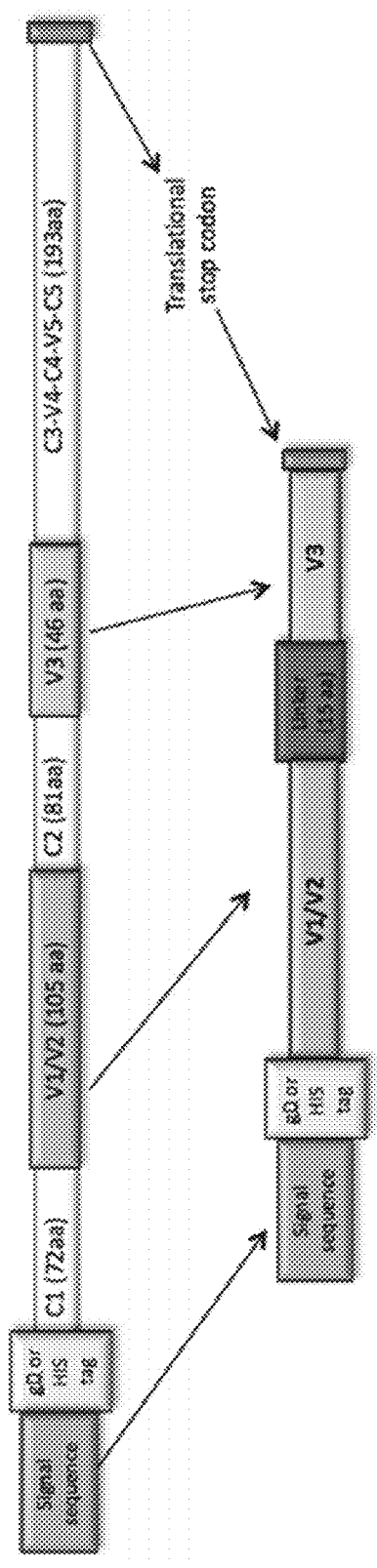
Figure 15:
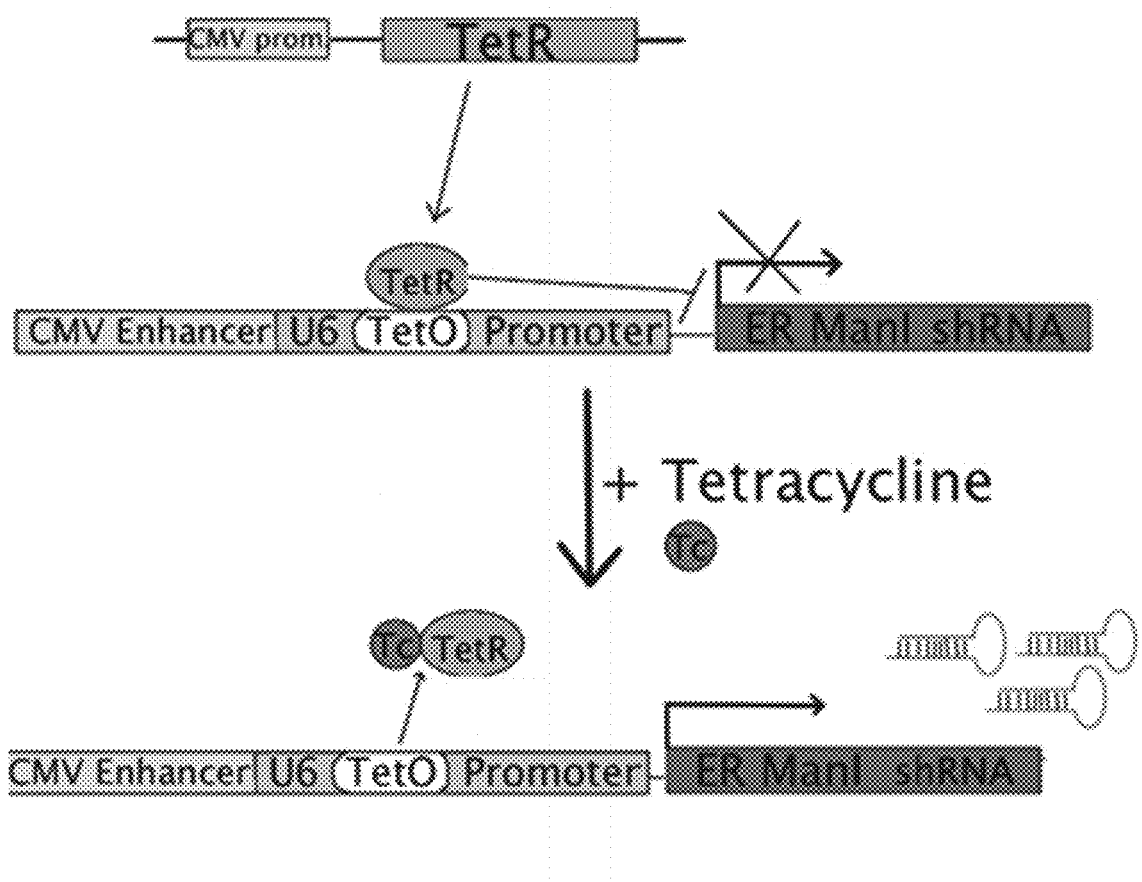
FIG. 15 A transcription unit directing expression of an shRNA to inhibit mannosidase I (ManI) expression.

The observation of strain-dependent differences in PG9 binding affinity, even with proteins produced in GnTI– cells, suggested that amino acids other than those previously identified as contact residues for PG9 (7, 27) affect the binding of PG9 to V1/V2 scaffolds. To identify these, a sequence alignment was constructed comparing sequences of scaffolds able to bind PG9 with sequences of scaffolds unable to bind (FIG. 3A). This alignment allowed us to identify amino acid polymorphisms, variations in loop length, and number of N-linked glycosylation sites that might affect the binding of PG9. Previous structural studies of the V1/V2 domain expressed as a glycopeptide fragment (16) or within trimeric gp140 complexes (28) showed that it adopts a four-stranded antiparallel β-sheet structure. The structure consists of strands designated A, B, C, and D, and the connecting loops (FIG. 3B). Strands B and C form a β-hairpin structure linked by a short turn region (FIGS. 3 B and C). The structure of PG9 co-crystallized with the V1/V2 domain shows the antibody interacts with the hydrophilic side of the β-hairpin structure. In the crystal structures, PG9 binding critically depends on contacts made with glycans at N156 and N160 as well as basic amino acids at 168, 169, and 171 (16, 27). Recognizing that PG9 interacts with the hairpin structure, we focused on amino acid changes that could potentially stabilize this interaction and enhance binding of this antibody. Previous studies of the V2 domain alone showed that PG9 binding to short synthetic glycopeptides could be improved by the addition of an extra disulfide bond that stabilized the hairpin structure (18). Because it was known that cross-strand interactions between side-chains and the turn region are important factors for hairpin formation and stability in other proteins (29-35), we sought to identify amino acid changes that would improve the formation of the hairpin structure. To accomplish this, we compared the sequences of scaffolds that exhibited strong binding with those that exhibited weak binding in the context of recent structural information (FIG. 3). We then systematically replaced multiple amino acids from the clade B 108060 scaffold, that exhibited low PG9 binding, with amino acids from the clade C, ZM233 and clade CRF01-AE, A244 scaffolds that exhibited higher affinity binding.

Effect of Amino Acid Mutations in the B and C Strands on PG9 Binding

We noted that the 108060 scaffold contained many of the amino acids required for PG9 binding, except for a critical contact at position 169 (16) where isoleucine (I) replaced a critical lysine (K). We found (FIG. 2F) that replacement of I for K at position 169 (I169K mutant) improved PG9 binding when expressed in GnTI– cells, but had no effect on binding to the scaffold produced in normal 293 cells. Because of its improved binding to PG9, the 108060-I169K mutant became our template for further mutational analysis. The next mutation introduced was E172V (FIG. 2G). This amino acid was selected for several reasons. First, valine is an amino acid frequently found in β-sheet structures (30). Valine, isoleucine, and threonine have a β-branched carbon that limits the conformations the main-chain backbone can adopt (30). Second, valine is a hydrophobic amino acid and can form cross-strand interactions with hydrophobic amino acids on opposing strands. In the B-C hairpin structure, V172 is in the middle of strand C and could potentially interact with F159 on strand B. Finally, V172 occurred within a sequence found in the C strand shown to be important for the binding of antibodies that correlated with protection in the RV144 HIV vaccine trial (21, 36). As shown in FIG. 2G, the combination of K169 and V172 (I169K/E172V) improved PG9 binding to the 108060 scaffold produced in GnTI– cells. Because position 172 is not a contact site for PG9, and is oriented on the opposite side of the PG9 contact surface, this residue appears to indirectly affect PG9 binding. Valine at 172 on the C strand appears likely to interact with F159 on the B strand, resulting in a hydrophobic interaction that may facilitate or stabilize the hairpin structure (FIGS. 3 B and C).

The I169K and E172V mutant of the 108060 scaffold became the new template for mutational analysis. We next selected the T161M polymorphism from the alignment for the next round of mutagenesis. We found this mutation did not improve binding to the V1/V2 scaffold expressed in GnTI– cells, but did show a small improvement to scaffold expressed in 293 cells (data not shown). Similar to the E172V polymorphism, T161M is oriented on the opposite side of the PG9 contact surface and does not interact directly with the antibody; thus the improvement in binding appears to be an indirect effect. Cross-strand hydrophobic interactions among F159, M161, and V172 were predicted to stabilize the hairpin structure and lead to better binding.

Previous studies have shown that PG9 and PG9-like antibodies do not always require the N156 glycosylation site in the V1/V2 domain for binding and neutralization (23, 37-41). However, the importance of this site had not been explored in the context of V1/V2 scaffolds. Based on the observation that ZM233 has an isoleucine at position 156, we removed the glycosylation site from the mutant 108060 V1/V2 scaffold by substitution of isoleucine for asparagine at 156. Interestingly, we found that the loss of the N-linked glycosylation site at N156 did not diminish PG9 binding. Rather, the N156I substitution resulted in a significant improvement in binding to the scaffold produced in normal 293 cells and a small improvement in binding to the scaffold produced in GnTI– cells (FIG. 2H).

Effect of Mutations in the B-C Turn on PG9 Binding

We next examined the importance of amino acid residues located at the B-C turn (residues 164 to 167) connecting the B and C strands. Amino acid sidechains in the turn region are key determinants of β-hairpin structure formation (32, 34, 35, 42, 43). Statistical analysis of amino acids found in hairpin turns shows a preference for small amino acids, such as glycine, and also for proline, asparagine, and aspartate (30, 44, 45). Based on the alignment, several amino acids in the B-C turn were identified as possibly being important for stabilizing this structure. Most Env sequences contain a glutamate (E) at 164 and aspartate (D) at 167, where E occupies the i position and D the i+3 position in the turn sequence. A hydrogen bond between the main chain carbonyl group from i position and the amino group from i+3 position helps stabilize the turn. However, the presence of two negatively charged amino acids at the i and i+3 positions may affect hairpin formation in the context of the V1/V2 scaffold. To investigate this, positions 164 and 167 were mutated to glycine (S164G/D167G; FIG. 2I). Mutating these sites serves several functions. First, glycine can adopt a wider range of Φ and ψ angles necessary for β-turns. Second, removing the negative amino acids occupying the i or i+3 positions may increase the turn propensity. Third, position 167 is a key site for the development of some PG9-like and strain-specific mAbs, and for mAbs dependent on quaternary structures of the V2 domain (39, 40, 46, 47). We found that incorporating glycines at positions 164 and 167 of the 108060 mutant enhanced PG9 binding with EC50's of 93.0 ng/ml for 293 cells and 6.8 ng/ml for GnTI– cells (FIG. 2I, Table S2).

To further investigate the role of the B-C turn, we evaluated another turn sequence. We substituted proline for serine at position 164 and glycine for leucine at position 165 (S164P/L165G). These replacements were selected from the literature rather than the alignment. Previous studies suggested that the proline-glycine combination is a strong promoter of hairpin formation (34, 48). Proline is statistically preferred at the i position for many common turn types (44, 45), and adding a proline introduces a kink into strand B that restricts the φ to −60. We found that the S164P/L165G mutant had PG9 binding similar to the S164G/D167G mutant. As shown in FIG. 2J and Table S2, an EC50 of 155.7 ng/ml was observed for 293F cells and 8.34 ng/ml for GnTI– cells.

Incorporation of Mutations that Improved PG9 Binding into V1/V2 Scaffolds of Other Virus Strains.

Next, we wanted to know if the mutations introduced in the 108060 V1/V2 scaffold would similarly be effective in V1/V2 scaffolds from other virus strains. For this purpose, we introduced the set of B and C strand and turn mutations (I169K, E172V, T161M, N156I, S164G, and D167G) that improved PG9 binding into V1/V2 scaffolds from the MN, JRFL-E168K, A244, and ZM233 isolates. As shown in FIGS. 2 B and C, no binding was observed with the wildtype MN and JRFL-E168K scaffolds expressed in 293 cells, and only a trace amount of binding was observed when expressed in GnTI– cells. When we incorporated these amino acid changes, we found a dramatic increase in binding ability (FIGS. 2 L and M). The EC50s for PG9 binding to MN and JRFL-E168K expressed in 293 cells increased from being undetectable to 27.4 and 47.3 ng/mL, respectively. When expressed in GnTI– cells the EC50s were 7.9 and 13.0 ng/mL. Incorporation of these mutations into the A244 V1/V2 scaffold similarly enhanced binding of PG9 to the scaffold produced in 293 cells and reduced the EC50 from 893.5 ng/mL to 99.1 ng/mL (FIG. 2N). The highest affinity binding for a scaffold expressed in 293 cells was observed for the ZM233 scaffold (FIG. 2O) where the EC50 of 77.1 ng/mL for the wild type scaffold was reduced to 2.27 ng/mL for the scaffold that incorporated the mutations in the B and C strands. Thus this scaffold expressed in 293 cells demonstrated affinity similar to the A244 and ZM233 scaffolds expressed in GnTI– cells. Interestingly, the scaffolds from the A244 isolate of gp120 were all monomers (FIG. S2) whereas the engineered scaffolds from the other strains were all dimers. Thus dimerization did not prevent binding of the scaffolds to PG9 with high affinity.

Glycan Dependence of PG9 Binding to Engineered V1/V2 Scaffolds

In other studies, we were interested in further exploring the glycan dependence of antibody binding to the engineered V1/V2 domain scaffolds. The 3-D structures suggest that PG9 possesses different and distinct sites for interacting with the mannose-5 glycans at N156 and N160 (16, 28). A similar two-site recognition mechanism is thought to be required for the 2G12 and PGT128 antibodies that also bind to glycan-dependent epitopes in gp120 (11, 26). To determine if a bispecific glycan interaction could enhance PG9 binding, we mutated the ZM233 isolate to add the N156 glycosylation site that is missing from this strain. The results of this experiment are shown in FIG. 2P. We found that addition of this site inhibited PG9 binding rather than enhancing it. Therefore, the interaction of PG9 with ZM233 is somewhat different than the interaction of this antibody with other scaffolds.

Another issue we wanted to explore was whether the binding of the engineered scaffolds to PG9 still depended on mannose-containing glycans or whether the mutations we introduced eliminated the glycan dependence by strengthening PG9 binding to the amino acid contacts in the V1/V2 scaffolds. The binding of PG9 normally depends on mannose-5 at position N156 and N160 for binding (16, 17). Indeed ~67% of the PG9 interaction surface is thought to be attributable to contacts on the antibody with glycans at N156 and N160 (16). Mannose-5 is an intermediate in the N-linked glycosylation pathway, and is not normally incorporated into mature glycoproteins that are exported through the normal secretion and export pathway. It has been postulated that the unusual glycans that occur on HIV-1 envelope protein result as a consequence of envelope trimerization in the endoplasmic reticulum where specific glycan positions are incompletely glycosylated due to conformational shielding or glycan masking (26). However, it would be surprising if these mechanisms could account for the incorporation of high mannose glycans at positions N156 and N160 in gp120 monomers, or in V1/V2 scaffolds where trimerization does not occur. Therefore, we wanted to determine whether the binding of engineered scaffolds still resulted from contacts between PG9 and high mannose glycans, or whether the mutations we incorporated may have overcome the requirement for antibody contacts with glycans in the V1/V2 scaffolds. To explore this possibility, we measured the binding of PG9 to the engineered MN and ZM233 scaffolds expressed in normal 293 cells and treated with endoglycosidase H (Endo H). Endo H cleaves high mannose and some hybrid N-linked oligosaccharides between the two N-acetylglucosamine residues in the diacetylchitobiose core. Endo H will not cleave complex, sialic acid-containing oligosaccharides that are typically incorporated when produced in normal 293 cells (9, 49-51). The results are shown in FIGS. 2Q and R. We found that the binding of both scaffolds was destroyed by treatment with Endo H. Therefore, PG9 binding to the engineered scaffolds still requires high mannose glycans for binding.

Kinetics and Affinity of PG9 Binding to V1/V2 Scaffolds

We next examined the kinetics and binding affinity of PG9 binding to the engineered scaffolds by surface plasmon resonance (SPR). PG9 was captured onto chips derivatized with goat anti-human Fc antibody at approximately 100 RU's, and the V1/V2 scaffolds were flowed over the antibody coated chip at various concentrations (Materials and Methods). We first measured PG9 binding to the wildtype (unmutated) A244 scaffold expressed in GnTI- cells. This gave the highest affinity binding of any wildtype scaffold, with a Kd of approximately 15 nM (FIG. 4A). We next examined the binding of engineered A244 V1/V2 produced in normal 293 cells (FIG. 4B) and found that the Kd was somewhat greater (49 nM) and exhibited a faster off-rate ($1.9 \times 10^{-3}$ s-1) than the wild type sequence expressed in GnTI- cells ($7.7 \times 10^{-4}$ s-1). We next measured the binding to the engineered ZM233 scaffold expressed in normal 293 cells (FIG. 4C) and observed a Kd of 33 nM. Thus the binding affinity of this scaffold to PG9 was somewhat higher than binding to the engineered A244 scaffold. Thus the engineered V1/V2 scaffolds represented a significant improvement over wildtype scaffolds, because they exhibited high affinity binding to PG9 even when expressed in normal 293 cells.

Discussion

Here we describe the development of V1/V2 glycopeptide scaffolds from three clades of HIV, all able to bind to the prototypic bN-mAb PG9 with high affinity when expressed in normal cell lines. This data is significant for several reasons. First, it shows that the glycan-dependent structure of the epitope recognized by PG9 can be replicated by engineered fragments (scaffolds) of the V1/V2 domain. Second, it shows that these scaffolds can be produced in normal cell lines of the type required for biopharmaceutical production and clinical testing without the need for GnTI- cells or expensive glycosylation inhibitors. Third, it identifies amino acids, distinct from the residues that serve as antibody contact sites, that appear to improve PG9 binding by stabilizing the B and C turn, and by improving hydrophobic interactions in the four-stranded V1/V2 domain β-sheet structure. Fourth, the development of V1/V2 scaffolds provides a potential solution for the poor immunogenicity of both glycan-dependent and glycan-independent epitopes in the V1/V2 domain such as the PG9 epitope and the epitope (residues 165-178) recognized by non-neutralizing antibodies that correlated with protection in the RV144 HIV vaccine trial (20-22, 36). Fifth, vaccines based on the scaffolds described eliminate the possibility of immunodominant antibody responses to decoy epitopes in other parts of the gp120 that represent the majority of antibodies elicited by HIV-1 vaccines developed to date. Finally, our scaffolds can be combined with scaffolds under development by other groups such as those targeting the glycan-independent epitope recognized by the VRC01 bNAb that prevents CD4 binding (52). As with antiviral drugs, it is likely that an effective HIV vaccine will need to simultaneously target at least three conserved sites of virus vulnerability in order to overcome the problem of virus variation and subsequent immune escape. The V1/V2 scaffolds described in this report represent at least one component of a multivalent vaccine.

These studies clearly show that it is possible to develop glycopeptide scaffolds able to bind PG9 with high affinity, and that this epitope can be replicated by scaffolds without the need for full length gp120 or trimeric envelope proteins, either of which can stimulate massive antibody responses to decoy epitopes. It has been reported that PG9 binding to SOSIP gp140 trimers from the BG505 strain of HIV-1 exhibited a Kd of approximately 11 nM (53). This binding affinity is approximately the same as that measured for the wildtype A244 V1/V2 scaffold produced in GnTI- cells (e.g. 15 nM) and somewhat lower than the Kds measured for the engineered A244 and ZM233 scaffolds expressed in normal 293 cells (33 nm and 49 nM, respectively). At this time, we do not know whether there is a threshold affinity required to stimulate the activation of PG9-like B receptors (BCRs), and whether a somewhat higher binding affinity is an advantage that overcomes the disadvantage of immunization with monomeric or trimeric envelope proteins that elicit a myriad of antibodies to decoy epitopes.

The scaffolds from the A244 and ZM233 isolates are particularly interesting because they were derived from two of the rare envelope proteins able to bind directly to inferred germline immunoglobulin precursor of PG9 (54). Therefore, these scaffolds should allow us to directly test the hypothesis that immunization with antigens that bind directly to BCRs representative of inferred germline genes is an advantage over the guided immunization strategy designed to elicit antibodies to epitopes recognized by other bNAbs (e.g., 2G12 and VRC01) that are unable to directly bind to inferred germline BCRs (3, 4, 55). However, little is known about the adjuvants and formulations effective in eliciting antibodies to glycan-dependent epitopes. Moreover, most experimental animal models lack the long CDRH3 domains commonly found in bNAbs to GDEs such as PG9. Thus immunization studies in humans with alternative formulations is likely to be the only way to characterize the utility of these immunogens (56). The studies described show that it is technically possible to produce scaffolds with the glycans required to bind bNAbs such as PG9 in cell lines suitable for biopharmaceutical production. Since these scaffolds possess the V1/V2 domain sequences recognized by antibodies that correlated with protection in the RV144 trial, possess the epitope recognized by the PG9 bNAb, and lack the immunodominant decoy epitopes recognized by non-protective antibodies, they provide a new approach to stimulate protective antibody responses to the V1V2 domain.

Materials and Methods

Construction of V1/V2 Scaffolds

Sequences of V1/V2 scaffolds were amplified by polymerase chain reaction (PCR) from genes encoding gp120 using standard methods. The genes encoding gp120s from the MN, A244, 108060 isolates have been previously described (57-59). The genes encoding Bal.01; CAP45.2.00.G3, SVPC16; ZM109F.PB4, SVPC13;

ZM197M.PB7, SVPC6; and ZM233M.PB6, SVPC9 were obtained from the NIH AIDS Reagent Program (Germantown, Md.). The gene encoding gp120 from JRFL that incorporated the E168K mutation required for PG9 binding was kindly provided by Dr. Dennis Burton (The Scripps Research Institute, La Jolla, Calif.). All V1/V2 scaffolds were expressed as described previously (19) by transient transfection in either 293 HEK cells (FreeStyle™ 293F; Invitrogen, Inc., Carlsbad, Calif.) or in 293 HEK cells deficient in N-acetylglucosaminyltransferase I (GnTI−) that limit N-linked glycans to mannose-5 containing glycan structures (Catalog number CRL-3022, American Type Culture Collection, Manassas, Va.). The V1/V2 fragments used for ELISA were all expressed as fusion proteins that possessed an N-terminal flag epitope of 27 amino acids from herpes simplex virus 1 glycoprotein D (gD-1) as described previously (19, 60, 61). All of the V1/V2 scaffolds incorporated short sequences from the C1 and C2 domain to preserve the disulfide bonded stem of the V1/V2 domain. Thus the sequences began at position 116 in the C1 domain and ended at position 207 in the C2 domain (HXB2 numbering). For initial screening of scaffolds with the wildtype sequences, PG9 binding studies were carried out with unpurified proteins present in growth conditioned cell culture media. The amount of protein in each supernatant was normalized by the binding of the 34.1 monoclonal antibody to the flag epitope. The scaffolds used for protein engineering were all purified by immunoaffinity chromatography with an anti-gD antibody. The scaffolds used for Biacore binding incorporated an N-terminal Strep-tag/6× Histidine-tag (IBA GmbH, Goettingen, Germany) fused to position 118. This tag allowed for purification by nickel-Sepharose affinity chromatography. The sequence of the tag was: HHHHHGSGSAWSHPQFEKG-SGLLEVP. The sequences of the V1/V2 domain of all of the scaffolds used in this study are provided in Table S1. Sequence numbering is provided with reference to HXB2 reference standard (GenBank AF033819).

Production and Purification of V1/V2 Scaffolds

The V1/V2 scaffolds were expressed by transient expression of either 293F cells or GnTI− 293 cells using polyethyleneimine in volumes ranging from 0.1 L to 2 L (62). Growth conditioned cell culture supernatants were harvested 3 or 4 days post transfection for assays or purification. For gD-tagged constructs, immunoaffinity chromatography was used to purify the proteins as described previously (19). To purify His tag constructs, HisTrap and StrepTactin sepharose high performance columns (GE Healthcare Biosciences) were used. Purified proteins were further purified by size exclusion chromatography (HiLoad Superdex 200 (26/60) column, GE Healthcare). All proteins were buffer exchanged into Tris buffered saline (TBS) and analyzed by SDS-PAGE using 4-12% precast gradient gels (Invitrogen).

Antibodies

The PG9 monoclonal antibody used in these studies was purchased from Polymun Scientific GmbH (Vienna, Austria). The 34.1 mouse monoclonal antibody, specific for the N-terminal gD flag epitope of HSV-1, was isolated in our laboratory and was used as a capture antibody in indirect ELISA assays. Mouse anti-His6× mAb clone AD1.1.10 was purchased from R&D systems (Minneapolis, Minn.). Human IgG1 isotype control mAb was purchased from Sigma-Aldrich (St. Louis, Mo.).

ELISAs to Measure Antibody Binding to V1/V2 Scaffolds

ELISA were used to measure PG9 binding to purified V1/V2 scaffold or unpurified V1/V2 scaffolds present in cell culture media. For both assays, microtiter plates (Nunc Maxisorp, Rochester, N.Y.) were coated with 2 µg/ml of 34.1 anti-gD antibody in PBS overnight at 4° C. The plates were then washed 4 times with PBS containing 0.05% Tween-20, and blocked for 1-2 hrs with PBS containing 1% BSA (blocking buffer). Purified V1/V2 scaffolds (10 µg/ml) or unpurified scaffolds contained in cell culture supernatants were added to each well. (Immuno-blotting was used to confirm unpurified scaffold expression and to normalize the amount of protein coated.) Serial dilutions of PG9 or an isotype matched control antibody were added to the V1/V2 scaffold coated plates at concentrations ranging from 10 µg/ml to 0.001 µg/ml. After washing, Fc specific peroxidase-conjugated goat anti-human IgG (AffiniPure, Jackson ImmunoResearch, West Grove, Pa.) was then added at a 1:5000 dilution. OPD substrate (Fisher Scientific, Pittsburgh, Pa.) was then added for 10 min and the reaction was stopped with 3 M H2SO4. The absorbance was measured at 490 nm. The plates were then read in a microtiter plate spectrophotometer (Spectramax 190, Molecular Devices, Sunnyvale, Calif.). All steps, except coating, were done at room temperature on a shaking platform; incubation steps were for 1 hr. All dilutions (except coating) were done in blocking buffer. Washes with PBS+0.05% Tween-20 (4×) were included after incubation steps.

Endoglycosidase H Digestion

Endo H cloned from *Streptomyces picatus* and expressed in *E. coli* was purchased from New England Biolabs (Boston, Mass.). The V1/V2 scaffolds treated with Endo H were digested under native conditions, without reduction or alkylation. Briefly, 30 µg of V1/V2 scaffold in 50 mM sodium citrate buffer pH 5.5 (G5 buffer) was digested with 500 U of Endo H overnight at 37° C. Mock digestions were run under the same conditions except Endo H was not included. The digestion products were analyzed by ELISA as described above and by polyacrylamide gel electrophoresis. Purified A244-rgp120 produced in normal or GnTI− cells served as positive and negative controls for the enzyme digestion.

Surface Plasmon Resonance

Kinetic analysis of V1/V2 scaffold binding to PG9 was carried out using a Biacore 3000 instrument (Protein and Nucleic Acid Facility, Stanford University). Human antibody capture kit (GE Healthcare/Biacore) was used to immobilize anti-human IgG Fc to a CM5 sensor chip using primary amine chemistry. Briefly, the carboxymethylated dextran surface was activated using EDC/NHS, anti-human IgG Fc was conjugated to the chip, and the reaction blocked using 1M ethanolamine-HCl. The running buffer HBS-EP was also used for antibody dilutions. Isotype control and PG9 were captured to 50-100 RU. Five concentrations of V1/V2 scaffold were tested. Analysis was done with BIA evaluation software and fit to a 1:1 Langmuir model. Background was subtracted from the isotype control.

GENERAL DISCLOSURES

All publications and patent applications cited herein are incorporated by reference for all purposes.

The terms "complementary" and "complementarity" refer to the natural binding of polynucleotides by base pairing. For example, the sequence "5' A-G-T 3'" bonds to the complementary sequence "3' T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands.

"Conservative amino acid substitutions" are those substitutions that, when made, least interfere with the properties of the original protein, i.e., the structure and especially the function of the protein is conserved and not significantly changed by such substitutions. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The term "derivative" refers to the chemical modification of a polypeptide sequence, or a polynucleotide sequence. Chemical modifications of a polynucleotide sequence can include, for example, replacement of hydrogen by an alkyl, acyl, hydroxyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

A "fragment" is a unique portion of a parent sequence which is identical in sequence to but shorter in length than the parent sequence. A fragment may comprise up to the entire length of the defined sequence, minus one nucleotide/amino acid residue. For example, a fragment may be at least 5, 10, 15, 20, 25, 30, 40, 50, 60, 75, 100, 150, 250 or at least 500 contiguous nucleotides or amino acid residues in length. Fragments may be preferentially selected from certain regions of a molecule. For example, a polypeptide fragment may comprise a certain length of contiguous amino acids selected from the first 250 or 500 amino acids (or first 25% or 50% of a polypeptide) as shown in a certain defined sequence. Clearly these lengths are exemplary, and any length that is supported by the specification, including the Sequence Listing, tables, and figures, may be encompassed by the present embodiments.

The phrases "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity between polynucleotide sequences may be determined using the default parameters of the CLUSTAL V algorithm as incorporated into the MEGALIGN version 3.12e sequence alignment program. This program is part of the LASERGENE software package, a suite of molecular biological analysis programs (DNASTAR, Madison Wis.). CLUSTAL V is described in Higgins, D. G. and P. M. Sharp (1989) CABIOS 5:151-153 and in Higgins, D. G. et al. (1992) CABIOS 8:189-191. For pairwise alignments of polynucleotide sequences, the default parameters are set as follows: Ktuple=2, gap penalty=5, window=4, and "diagonals saved"=4. The "weighted" residue weight table is selected as the default. Percent identity is reported by CLUSTAL V as the "percent similarity" between aligned polynucleotide sequence pairs. Alternatively, a suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403-410). The "BLAST 2 Sequences" tool can be used for both blastn and blastp (discussed below). BLAST programs are commonly used with gap and other parameters set to default settings. For example, to compare two nucleotide sequences, one may use blastn with the "BLAST 2 Sequences" tool Version 2.0.9 (May 7, 1999) set at default parameters. Such default parameters may be, for example: Matrix: BLOSUM62; Reward for match: 1; Penalty for mismatch: −2; Open Gap: 5 and Extension Gap: 2 penalties; Gap x drop-off: 50; Expect: 10; Word Size: 11; Filter: on.

Percent identity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the hydrophobicity and acidity at the site of substitution, thus preserving the structure (and therefore function) of the polypeptide.

Percent identity between polypeptide sequences may be determined using the default parameters of the CLUSTAL V algorithm as incorporated into the MEGALIGN version 3.12e sequence alignment program (described and referenced above). For pairwise alignments of polypeptide sequences using CLUSTAL V, the default parameters are set as follows: Ktuple=1, gap penalty=3, window=5, and "diagonals saved"=5. Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

"Hybridization" refers to the process by which a polynucleotide strand anneals with a complementary strand through base pairing under defined hybridization conditions. Specific hybridization is an indication that two nucleic acid sequences share a high degree of identity. Specific hybridization complexes form under permissive annealing conditions and remain hybridized after the "washing" step(s). The washing step(s) is particularly important in determining the stringency of the hybridization process, with more stringent conditions allowing less non-specific binding, i.e., binding between pairs of nucleic acid strands that are not perfectly matched. Permissive conditions for annealing of nucleic acid sequences are routinely determinable by one of ordinary skill in the art and may be consistent among hybridization experiments, whereas wash conditions may be varied among experiments to achieve the desired stringency, and therefore hybridization specificity. Permissive annealing conditions occur, for example, at 68° C. in the presence of about 6×SSC, about 1% (w/v) SDS, and about 100 µg/ml denatured salmon sperm DNA.

Generally, stringency of hybridization is expressed, in part, with reference to the temperature under which the wash step is carried out. Generally, such wash temperatures are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. An equation for calculating $T_m$ and conditions for nucleic acid hybridization are well known and can be found in Sambrook et al., 1989, *Molecular Cloning: A Laboratory Manual*, 2$^{nd}$ ed., vol. 1-3, Cold Spring Harbor Press, Plainview N.Y.; specifically see volume 2, chapter 9.

High stringency conditions for hybridization between polynucleotides of the present invention include wash conditions of 68° C. in the presence of about 0.2×SSC and about 0.1% SDS, for 1 hour. Alternatively, temperatures of about 65° C., 60° C., 55° C., or 42° C. may be used. SSC concentration may be varied from about 0.1 to 2×SSC, with SDS being present at about 0.1%. Typically, blocking reagents are used to block non-specific hybridization. Such blocking reagents include, for instance, denatured salmon sperm DNA at about 100-200 µg/ml. Organic solvent, such as formamide at a concentration of about 35-50% v/v, may also be used under particular circumstances, such as for RNA:DNA hybridizations. Useful variations on these wash conditions will be readily apparent to those of ordinary skill in the art. Hybridization, particularly under high stringency conditions, may be suggestive of evolutionary similarity between the nucleotides. Such similarity is strongly indicative of a similar role for the nucleotides and their encoded polypeptides.

The phrases "nucleic acid" and "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material.

"Operably linked" refers to the situation in which a first nucleic acid sequence is placed in a functional relationship with the second nucleic acid sequence. For instance, a promoter is operably linked to a coding sequence if the promoter affects the transcription or expression of the coding sequence. Generally, operably linked DNA sequences may be in close proximity or contiguous and, where necessary to join two protein coding regions, in the same reading frame.

A "variant" of a particular nucleic acid sequence is defined as a nucleic acid sequence having at least 40% sequence identity to the particular nucleic acid sequence over a certain length of one of the nucleic acid sequences using blastn with the "BLAST 2 Sequences" tool Version 2.0.9 (May 7, 1999) set at default parameters. Such a pair of nucleic acids may show, for example, at least 50%, at least 60%, at least 70%, at least 80%, at least 85%, at least 90%, at least 95% or at least 98% or greater sequence identity over a certain defined length. A variant may be described as, for example, an "allelic" (as defined above), "splice," "species," or "polymorphic" variant. A splice variant may have significant identity to a reference molecule, but will generally have a greater or lesser number of polynucleotides due to alternate splicing of exons during mRNA processing. The corresponding polypeptide may possess additional functional domains or lack domains that are present in the reference molecule. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one nucleotide base. The presence of SNPs may be indicative of, for example, a certain population, a disease state, or a propensity for a disease state.

A "variant" of a particular polypeptide sequence is defined as a polypeptide sequence having at least 40% sequence identity to the particular polypeptide sequence over a certain length of one of the polypeptide sequences using blastp with the "BLAST 2 Sequences" tool Version 2.0.9 (May 7, 1999) set at default parameters. Such a pair of polypeptides may show, for example, at least 50%, at least 60%, at least 70%, at least 80%, at least 90%, at least 95%, or at least 98% or greater sequence identity over a certain defined length of one of the polypeptides.

The invention claimed is:

1. A polypeptide comprising of V1/V2 domain of the HIV-1 envelope protein gp120 fused to V3 stem domain of the HIV-1 glycoprotein gp120, wherein the polypeptide does not include the C2 domain of the HIV-1 glycoprotein gp120.

2. The polypeptide of claim 1 expressed as a fusion protein in mammalian cells wherein a signal sequence is fused to the N-terminus, and a flag epitope is incorporated at the mature N-terminus or C-terminus of the scaffold protein.

3. The polypeptide of claim 2 wherein the polypeptide is expressed in a cell line lacking the N-acetlylglucosaminyl transferase I gene and the mannosidase I gene is silenced by an sHRNA.

4. The polypeptide of claim 2 wherein the polypeptide is expressed in a cell line lacking the N-acetlylglucosaminyl transferase I gene and the mannosidase I gene is inhibited by a glycosylation inhibitor.

5. The polypeptide of claim 4 wherein glycosylation inhibitor is kifunensine.

6. The polypeptide of claim 1 comprising the amino acid sequence set forth in:

```
SEQ ID No. 3:
MGGAAARLGAVILFVVIVGLHGVRGKYALADASLKMADPNRFRGKDLPVL

DQLLEVPLKPAVKLTPPCVTLHCTNANLTKANLTNVNNRTNVSNIIGNIT

DEVRNCSFNMTCELRDKKQKVHALFYKLDIVPIEDNNDSSEYRLINCNTS

VIKQAAPKISFDPGGGGSGGGGSGGGGSVINCTRPSNNTRTSITCGPGQV

FYRTGDIIGDIRKAYCNISGTEWN*.
```

7. The polypeptide of claim 1, comprising a purification tag at the N-terminus or the C-terminus of the polypeptide.

8. The polypeptide of claim 7, wherein the purification tag comprises herpes simplex virus glycoprotein D or hexa-histidine.

9. The polypeptide of claim 7, wherein the polypeptide is expressed in a mammalian cell line lacking the N-acetlylglucosaminyl transferase I gene and the mannosidase I gene is silenced by an shRNA.

10. The polypeptide of claim 7, wherein the polypeptide is expressed in a mammalian cell line lacking the N-acetlylglucosaminyl transferase I gene and the mannosidase I gene is inhibited by a glycosylation inhibitor.

11. The polypeptide of claim 10, wherein glycosylation inhibitor is kifunensine.

12. The polypeptide of claim 1, wherein the polypeptide lacks C1, C3, V4, V5, and C5 domains.

13. The polypeptide of claim 1, wherein the V1/V2 domain is linked to the V3 stem domain via a flexible linker.

14. A method of immunization comprising a primary and a booster immunization, wherein both primary and booster immunizations comprise administration of the polypeptide of claim 1.

15. The method of claim 14 wherein the primary immunization further comprises administration of monomeric gp120 or trimeric gp140 possessing the glycans required for the binding of broadly neutralizing antibodies from the PG9, PGT121, and PGT128 families.

16. The method of claim 15 wherein the polypeptide is formulated in a non-toxic immunostimulatory adjuvant.

17. The method of claim 16 wherein the non-toxic immunostimulatory adjuvant is selected from alum, MF59, lipid A, and a GC rich synthetic DNA sequences.

* * * * *